(12) United States Patent
Mottram et al.

(10) Patent No.: US 10,695,211 B2
(45) Date of Patent: Jun. 30, 2020

(54) CRANIAL REMOULDING ORTHOSIS AND METHOD OF MANUFACTURE THEREOF

(71) Applicants: Technology in Motion Ltd, Leeds West Yorkshire (GB); ING Corporation spol. s.r.o., Frýdlant nad Ostravici (CZ)

(72) Inventors: Stephen Mottram, Leeds West Yorkshire (GB); Jiri Rosicky, Frýdlant nad Ostravici (CZ)

(73) Assignees: Technology in Motion Ltd, Leeds West Yorkshire (GB); ING Corporation spol. s.r.o, Frýdlant nad Ostravici (CZ)

( * ) Notice: Subject to any disclaimer, the term of this patent is extended or adjusted under 35 U.S.C. 154(b) by 289 days.

(21) Appl. No.: 15/754,340

(22) PCT Filed: Sep. 6, 2016

(86) PCT No.: PCT/GB2016/052744
§ 371 (c)(1),
(2) Date: Feb. 22, 2018

(87) PCT Pub. No.: WO2017/042550
PCT Pub. Date: Mar. 16, 2017

(65) Prior Publication Data
US 2019/0015238 A1    Jan. 17, 2019

(30) Foreign Application Priority Data

Sep. 8, 2015   (GB) .................................. 1515877.7

(51) Int. Cl.
*A61F 5/00*     (2006.01)
*A61F 5/058*    (2006.01)
(Continued)

(52) U.S. Cl.
CPC ............ *A61F 5/05891* (2013.01); *A42B 3/00* (2013.01); *A61B 34/10* (2016.02); *A61F 5/3707* (2013.01)

(58) Field of Classification Search
CPC .................................................... A61F 5/05891
(Continued)

(56) References Cited

U.S. PATENT DOCUMENTS 2,391,335 A * 12/1945 O'Brien ................... A42B 3/00
                                                                              2/425
6,052,849 A    4/2000 Dixon et al.
(Continued)

FOREIGN PATENT DOCUMENTS

GB        2490894 A       11/2012
JP     2014169510 A  *  9/2014  ........... A61F 5/3707
(Continued)

OTHER PUBLICATIONS

International Search Report and Written Opinion of the International Searching Authority for International Application No. PCT/GB2016/052744, entitled: "Cranial Remoulding Orthosis and Method of Manufacture Thereof," dated Nov. 28, 2016.

*Primary Examiner* — Kim M Lewis
(74) *Attorney, Agent, or Firm* — Hamilton, Brook, Smith & Reynolds, P.C.

(57) ABSTRACT

An orthosis (10) for correcting deformities in the head shape of babies and young children includes a mesh layer (20). The mesh layer (30) includes regions of varying stiffness in the mesh layer that are adapted to apply varying pressure to a wearer's head, so as to restrict undesirable growth and allow desired growth to correct the deformities. Accordingly, the mesh layer (30) provides a layer of uniform thickness but variable stiffness, so that a lightweight means of applying appropriate pressure to the wearer's head is provided. The mesh layer (30) can be manufacturer by 3D printing, based on a scan of the wearer's head.

16 Claims, 19 Drawing Sheets

(51) Int. Cl.
  *A61B 34/10*  (2016.01)
  *A42B 3/00*  (2006.01)
  *A61F 5/37*  (2006.01)

(58) Field of Classification Search
  USPC .......................................................... 602/17
  See application file for complete search history.

(56) References Cited

U.S. PATENT DOCUMENTS

| | | |
|---|---|---|
| 2004/0179728 A1 | 9/2004 | Littlefield et al. |
| 2006/0224098 A1 | 10/2006 | Uetake et al. |
| 2008/0184489 A1 | 8/2008 | Pham |
| 2009/0316965 A1 | 12/2009 | Mailling et al. |
| 2010/0138193 A1 | 6/2010 | Summit et al. |
| 2012/0296249 A1 | 11/2012 | Gordon et al. |
| 2013/0289459 A1* | 10/2013 | Bernardoni ......... A61F 5/05891 602/17 |
| 2014/0201889 A1 | 7/2014 | Pietrzak et al. |
| 2014/0371645 A1 | 12/2014 | Sakamoto et al. |

FOREIGN PATENT DOCUMENTS

| | | |
|---|---|---|
| WO | 9908628 A1 | 2/1999 |
| WO | 2014080217 A1 | 5/2014 |
| WO | 20140133091 A1 | 9/2014 |
| WO | 2017042550 A1 | 3/2017 |

\* cited by examiner

CRANIAL REMOULDING ORTHOSIS AND METHOD OF MANUFACTURE THEREOF

This application is the U.S. National Stage of International Application No. PCT/GB2016/052744, filed Sep. 6, 2016, which designates the U.S., published in English, and claims priority under 35 U.S.C. § 119 or 365(c) to GB Application No. 1515877.7, filed Sep. 8, 2015. The entire teachings of the above applications are incorporated herein by reference.

FIELD

This invention relates to an orthosis, particularly an orthosis for correcting deformities in the head shape of babies and young children.

BACKGROUND

In early infancy (0 to 24 months), the skull is made up of several separate 'plates' of bone, connected by flexible ligaments known as sutures. These sutures are present to allow normal birth and to allow the skull to develop as the infant brain grows. The plates retain some flexibility throughout childhood and as the child ages, the bones fuse together and create a permanent skull shape that cannot change.

However, a skull in infancy is soft enough to be deformed by constant external pressure due to the head being in one position on a firm surface for long periods. Such deformation is referred to as Flat Head Syndrome, or Deformational Plagiocephaly—an umbrella term for several related Head Shape Deformities including Plagiocephaly (an asymmetric flattening to the side of the head), Brachycephaly (a wide head shape with a flat back of the head) and Scaphocephaly or Dolichocephaly (a long thin head shape). The most usual presentation is a brachycephaly with some degree of plagiocephaly, sometimes known as a combination head shape deformity. One way of reducing the severity of such a condition is to provide specially shaped pillows, cushions or mattresses that are designed to minimise the development of a flat head. However, once a baby starts to roll onto its side or to be able to wriggle and move away from the pillow, usually at 3 to 5 months of age, they become minimally effective.

Occasionally, one or more of the sutures between the bone plates is prematurely fused, known as craniosynostosis and this can also cause a head shape deformity. This condition must be corrected by either open scalp or minimally invasive surgery.

In more severe cases of Head Shape Deformity or following surgery to resolve a Craniosynostisis, the infant is fitted with a helmet which gently allows the head shape to grow back towards normality. Typically, the helmets are made from a firm outer shell with a closed cell foam lining. The internal shape of the closed cell foam lining is precisely formed using the following method. A 3D photographic scan is taken of the infant's head shape and this is saved as a computer file. The file is then used to carve a polyurethane foam mould which is modified to a normalised head shape. The modifications can either be done by Computer Aided Design (CAD) or by manually adding plaster or a similar material. The helmet that the infant wears is formed over the modified mould shape and the internal shape comprises contours and recesses that are shaped so as to contact the infant's head in some regions, whilst providing regions where there is a void to allow desired growth.

Although successful in treatment, this type of helmet has several significant drawbacks. The manufacturing process is time consuming and wasteful of materials and energy. There are difficulties in achieving adequate control with large modifications to the mould shape, causing areas of undesirable high pressure and rotation of the helmet. The helmets require frequent internal modifications to allow graduated control and growth. These modifications break the smooth internal surface and cause it to be rough. The closed cell foam liner has high thermal insulating and non-porous characteristics which can cause the infants to sweat excessively, particularly in the initial stages of treatment. There is a high skill level required, both in manufacturing the helmet and in treating the infant. Parents also have a steep learning curve in initiating the treatment for their infant. Some parents report that their infant has difficulties in sleeping with the helmet in place (the helmet must be worn day and night).

It is the aim of this invention to address at least some of the above-mentioned difficulties, and any other difficulties that will be apparent from the description below. It is a further aim of this invention to provide a cost effective, efficacious and hygienic orthosis for correcting head deformities, and an efficient and cost effective method of manufacturing the same.

SUMMARY

According to the present invention there is provided an apparatus and method as set forth in the appended claims. Other features of the invention will be apparent from the dependent claims, and the description which follows.

According to a first aspect of the invention there is provided an orthosis for correcting head deformities, the orthosis comprising a mesh layer, wherein regions of varying stiffness in the mesh layer are adapted to apply varying pressure to a wearer's head, so as to restrict undesirable growth and allow desired growth to correct the deformities.

Preferably, the regions of varying stiffness comprises at least one region of increased flexibility, preferably to allow growth of a wearer's head in an area corresponding to the at least one region of increased flexibility. Preferably, the regions of varying stiffness comprises at least one region of decreased flexibility, preferably to constrain growth of the wearer's head in an area corresponding to the at least one region of decreased flexibility. Preferably, the at least one region of increased flexibility comprises a less dense portion of the mesh. Preferably, the at least one region of increased flexibility comprises a first mesh structure having increased flexibility. Preferably, the at least one region of decreased flexibility comprises a less dense portion of the mesh. Preferably, the at least one region of decreased flexibility comprises a second mesh structure having increased stiffness.

Preferably, the mesh layer is formed from a plurality of body elements and a plurality of openings defined by the body elements. Preferably, less of the material forming the body elements or a material with increased flexibility is present in the at least one region of increased flexibility than in the at least one region of decreased flexibility. Preferably, the ratio of the area defined by the openings compared to the area defined by the body elements or the flexibility of the material is greater in the at least one region of increased flexibility than in the at least one region of decreased flexibility. Preferably, the openings are larger in the at least one region of increased flexibility than in the at least one region of decreased flexibility. Preferably, more openings are present in the at least one region of increased flexibility than in the at least one region of decreased flexibility.

Preferably, the mesh layer comprises an auxetic structure, preferably having a negative Poisson's ration. Preferably, the auxetic structure comprises a two-dimensional pattern. Alternatively, the auxetic structure comprises a repeating three-dimensional pattern.

Advantageously, the mesh layer provides a layer of uniform thickness but variable stiffness, so that a convenient, lightweight means of applying appropriate pressure to the wearer's head is provided.

Preferably, the orthosis further comprises an outer layer that defines the exterior shape of the orthosis, wherein the mesh layer is disposed within the outer layer. Preferably the outer layer is substantially rigid. Advantageously, the outer layer provides protection to the head of the wearer and supports the other components of the orthosis.

Preferably, the orthosis comprises a plurality of ventilation apertures. Preferably, the ventilation apertures are disposed in the surface of the outer layer. More preferably, the ventilation apertures are disposed substantially uniformly on the surface of the outer layer. Advantageously, the increased ventilation ensures the wearer's head does not overheat.

Preferably, the mesh layer and the outer layer are arranged such that they are separated by a gap. Preferably, the gap is substantially from 0 mm to 30 mm, more preferably from 5 mm to 25 mm, more preferably from 10 mm to 20 mm, most preferably 15 mm.

Preferably, the orthosis comprises two portions and a fastening means to secure the two portions together, thereby securing the orthosis to the wearer's head. More preferably, the two portions are connected by a hinge, preferably a living hinge. Preferably, the fastening means comprises a length of hook and loop fastener material disposed on one of the portions, and a looping portion configured to receive the fastener material disposed on the other of the portions. Alternatively, the fastening means comprises at least one cable disposed around the circumference of the orthosis and a tightening means configured to tighten the at least one cable. The fastening means provides a convenient mechanism for both securing the orthosis on the head of the wearer and loosening the orthosis sufficiently for easy fitting and removal.

Preferably, the orthosis comprises one or more pads disposed between the mesh layer and the outer layer. The pads provide a means of adjusting the pressure applied to the wearer's head, and also help to prevent rotation of the orthosis once fitted.

Preferably, the orthosis comprises a plurality of cushioning elements. Preferably, each cushioning element is resiliently deformable, preferably in a substantially radial direction with respect to the wearer's head. Preferably, the cushioning elements are disposed on an interior surface of the mesh layer or the outer layer. Preferably, the cushioning elements are formed integrally with the mesh layer or outer layer. Preferably, the cushioning elements comprise a resiliently deformable spring having a cushion portion attached to an end thereof, wherein the cushion portion is adapted to receive pressure exerted by movement of the wearer's head. Advantageously, the cushioning elements act to provide cushioning to the wearer and improve the fit of the orthosis without exceeding capillary pressure at any one point on the wearer's head.

Preferably, the orthosis comprises a liner disposed inside the mesh layer. Preferably, the liner is a padded liner. Preferably, the liner is breathable. Preferably, the liner is self-wicking. Preferably, the liner is detachable from the orthosis. More preferably, the liner is washable. Preferably, the liner is resiliently deformable such that it is biased into a shape that securely retains it within the orthosis. Preferably, the liner is attached to the orthosis by attachment means. The liner increases the comfort of the wearer, and is easy to clean; thereby ensuring the orthosis is hygienic.

Preferably, the orthosis comprises at least one sensor arranged to measure a condition of the orthosis or the wearer. Preferably, the condition is at least one of a measurement of depth or distance between the mesh layer and outer layer, acceleration of the orthosis, a temperature in the orthosis, a humidity in the orthosis, a spatial position and/or orientation of the orthosis or a heart rate of the wearer. Preferably, the sensor/sensors is/are disposed on a side aspect of the orthosis, preferably in a position optimal for monitoring the required condition.

Preferably, the orthosis comprises a communication interface, operable to communicate sensor readings measured by the sensor/sensors to a monitoring device. Preferably, the communication interface comprises a passive interface operable to be read, preferably wirelessly, by the monitoring device. Alternatively, the communication interface comprises an active interface, operable to actively transmit the sensor readings to the monitoring device. The communication interface and the monitoring device may communicate via one or more of Near-field Communication (NFC), Radio-frequency identification (RFID), Bluetooth® Low Energy (BLE), Bluetooth®, Wi-Fi or a cable attachable to a port on the orthosis.

Preferably, the monitoring device comprises a communication interface operable to transfer the sensor readings to a user device. Alternatively, the monitoring device may be configured to transfer the sensor readings to a server, wherein the user device is configured to retrieve the sensor readings from the server. Preferably, the user device is a smart phone, tablet or personal computer. Preferably, the user device comprises an application, operable to display the sensor readings. Preferably, the user device is configured to be operated by a parent, therapist or medical professional.

Preferably, the orthosis, more preferably, sensor/sensors comprise a memory operable to store a plurality of a sensor readings captured over time. Preferably, the orthosis comprises a controller operable to capture sensor readings at predetermined time intervals and store them in the memory. Preferably, the controller is operable to delete sensor readings stored in the memory that have been successfully received by the monitoring device.

Preferably, the orthosis comprises a cover movable from a first position, in which the sensor is covered by the cover, to a second position, in which the sensor is exposed. Preferably, the cover is attached to the orthosis such that it is not removable therefrom.

According to a second aspect of the invention there is provided a method of manufacturing an orthosis for correcting head deformities comprising forming a mesh layer, wherein regions of varying stiffness in the mesh layer are adapted to apply varying pressure to a wearer's head, so as to restrict undesirable growth and allow desired growth to correct the deformities.

Preferably, the method comprises forming the mesh layer based on a virtual 3D model. Preferably, the virtual 3D model is based on measurements of the wearer's head, preferably established by means of a 3D scan. Preferably, the virtual 3D model is modified to so that the shape includes areas where growth is allowed or growth is restricted, respectively corresponding to regions of the mesh layer comprising regions of increased or decreased flexibility.

Preferably, the virtual 3D model is modified by the application of a predefined routine. Accordingly, the shape of a mesh layer suitable for correcting the particular head deformities of the wearer can be easily established.

Preferably, the mesh layer is formed using an additive manufacturing means, preferably a 3D printer. Preferably, the mesh layer is formed using a material that is suitable for prolonged contact with the skin of the wearer without irritation. Accordingly, a mesh layer suitable for the particular needs of an individual wearer can be easily manufactured.

Preferably, the method comprises inserting the mesh layer into an outer layer. Preferably, the outer layer is formed using the additive manufacturing means, preferably the 3D printer. This allows the dimensions of the outer layer to be easily customised based on the head shape of the wearer. Alternatively, the outer layer is formed by injection moulding or plastic thermoforming. Preferably, the mesh layer and the outer layer are secured together by one or more of hook and loop fastener material, click lock attachments or pin and hole type fastenings. This enables cost-effective production of the outer layer in one or more standard sizes, with only the mesh layer being specifically adapted for the wearer's head. Alternatively, the method comprises forming the outer layer and the mesh layer concurrently, preferably in a nested arrangement, preferably using the additive manufacturing means.

Preferably, the method comprises inserting pads between the outer layer and the mesh layer. The pads provide a means of adjusting the pressure applied to the wearer's head, and also help to prevent rotation of the orthosis once fitted.

Preferably, one or both of the outer layer and the mesh layer are formed in a multi-coloured pattern. Preferably, a surface print, embossed pattern or pierced pattern is applied to the outer layer. Accordingly, the orthosis is more visually appealing to the infant wearer.

Preferably, the method comprises inserting a liner into the orthosis. Preferably, the liner is flexible. Preferably, the liner is formed using a material that is suitable for prolonged contact with the skin of the wearer without irritation. The liner increases the comfort of the wearer and hygiene during treatment.

Further preferred features of the components manufactured in the method of the second aspect are defined hereinabove in relation to the first aspect and may be combined in any combination.

According to a third aspect of the invention there is provided a computer-readable medium having computer-executable instructions recorded thereon that, when executed, cause a 3D printer to print a mesh layer for an orthosis for correcting head deformities, wherein regions of varying stiffness in the mesh layer are adapted to apply varying pressure to a wearer's head, so as to restrict undesirable growth and allow desired growth to correct the deformities.

Preferably, the instructions, when executed, cause the 3D printer to print an outer layer for an orthosis. More preferably, the instructions case the 3D printer to print the outer layer and the mesh layer concurrently, preferably in a nested arrangement.

Further preferred features of the components required in the computer-readable medium of the third aspect are defined hereinabove in relation to the first and second aspects and may be combined in any combination.

According to a fourth aspect of the present invention there is provided a system for monitoring an orthosis, comprising the orthosis and a monitoring device, wherein the orthosis comprises at least one sensor arranged to measure a condition of the orthosis or wearer and a communication interface operable to communicate sensor readings measured by the sensor/sensors to the monitoring device, and the monitoring device comprises at least one sensor interface operable to receive sensor readings from the orthosis.

Preferably, the condition is at least one of a measurement of depth or distance between two layers of the orthosis, an acceleration of the orthosis, a temperature in the orthosis, a humidity in the orthosis, a spatial position/orientation of the orthosis or a heart rate of the wearer.

Preferably, the communication interface comprises a passive interface operable to be read, preferably wirelessly, by the at least one sensor interface. Alternatively, the communication interface comprises at least one active interface, operable to actively transmit the sensor readings to the at least one sensor interface. The communication interface and the at least one sensor interface may communicate via one or more of Near-field Communication (NFC), Radio-frequency identification (RFID), Bluetooth® Low Energy (BLE), Bluetooth®, Wi-Fi or at least one cable attachable to a port on the orthosis.

Preferably, the orthosis, more preferably the sensor, comprises a memory operable to store a plurality of sensor readings captured over time. Preferably, the orthosis comprises a controller operable to capture sensor readings at predetermined time intervals and store them in the memory. Preferably, the controller is operable to delete sensor readings stored in the memory that have been successfully received by the monitoring device.

Preferably, the monitoring device comprises a communication interface operable to transfer the sensor readings to a user device. Alternatively, the communication interface is operable to transfer the sensor readings to a server, wherein the user device is configured to retrieve the sensor readings from the server. Preferably, the user device is a smart phone, tablet or personal computer. Preferably, the user device comprises an application, operable to display the sensor readings. Preferably, the user device is configured to be operated by a parent, therapist or medical professional. Preferably, the system comprises the user device.

Preferably, the system comprises at least one sensor device, attachable to a part of the wearer's body. Preferably, the at least one sensor device is attachable via a strap, by direct placement on the body part or by adhesive. Preferably, each sensor device comprises a sensor arranged to measure a condition of the wearer or the sensor device, and a communication interface operable to communicate sensor readings measured by the sensor device to the monitoring device. Preferably, the sensor device comprises a positional sensor, operable to determine the spatial position of the sensor device, preferably with respect to the orthosis and/or other sensor devices. Preferably, the sensor device comprises a memory operable to store a plurality of a sensor readings captured over time. Preferably, the sensor device comprises a controller operable to capture sensor readings at predetermined time intervals and store them in the memory. Preferably, the controller is operable to delete sensor readings stored in the memory that have been successfully received by the monitoring device.

Further preferred features of the components required in the system of the fourth aspect are defined hereinabove in relation to the first, second and third aspects and may be combined in any combination.

According to a fifth aspect of the present invention there is provided an orthosis comprising at least one sensor arranged to measure a condition of the orthosis or wearer and a communication interface operable to communicate sensor readings measured by the sensor/sensors to a monitoring device.

Further preferred features of the components required in the orthosis of the fifth aspect are defined hereinabove in relation to the previous aspects and may be combined in any combination.

According to a sixth aspect of the present invention there is provided a monitoring device at least one sensor interface operable to receive sensor readings from an orthosis.

Further preferred features of the components required in the monitoring device of the sixth aspect are defined hereinabove in relation to the previous aspects and may be combined in any combination.

BRIEF DESCRIPTION OF DRAWINGS

For a better understanding of the invention, and to show how embodiments of the same may be carried into effect, reference will now be made, by way of example, to the accompanying diagrammatic drawings in which.

Figure 1A:
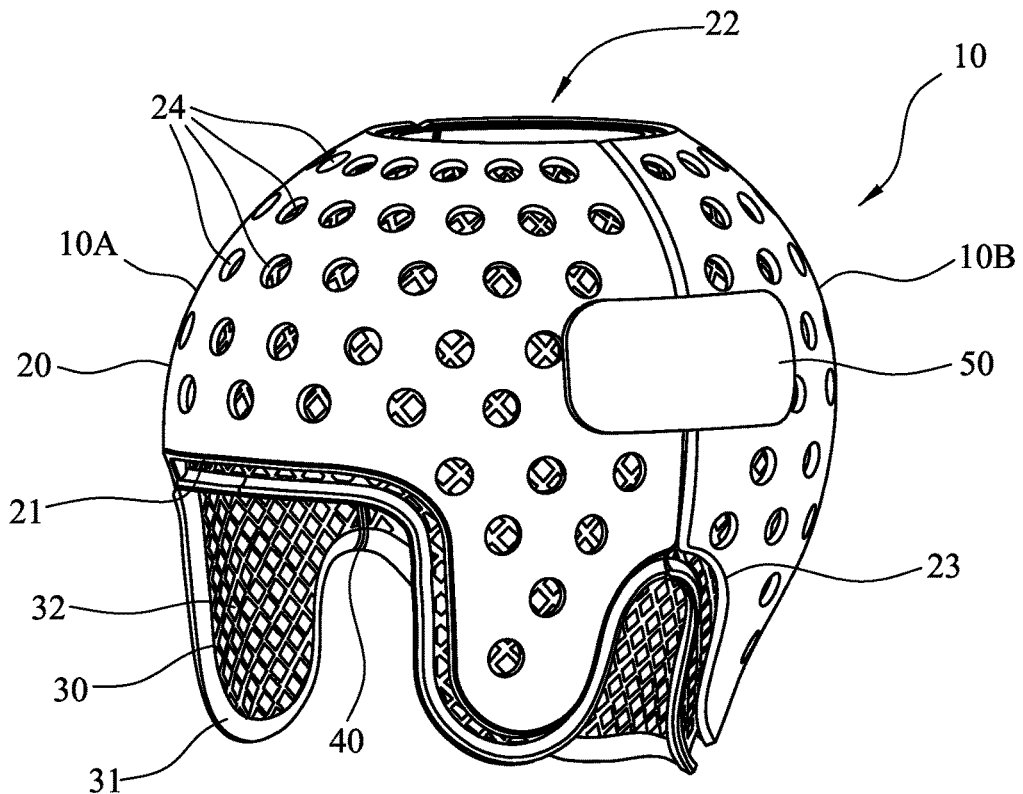
FIGS. 1A, 1B and 1C are respectively a perspective view, a side view and a front view of an orthosis according to an embodiment of the invention.

In the drawings, corresponding reference characters indicate corresponding components. The skilled person will appreciate that elements in the figures are illustrated for simplicity and clarity and have not necessarily been drawn to scale. For example, the dimensions of some of the elements in the figures may be exaggerated relative to other elements to help to improve understanding of various example embodiments. Also, common but well-understood elements that are useful or necessary in a commercially feasible embodiment are often not depicted in order to facilitate a less obstructed view of these various example embodiments

DESCRIPTION OF EMBODIMENTS

In overview, embodiments of the present invention provide an orthosis for correcting head deformities, comprising a variably flexible layer, which is stiffer in regions where growth is to be restrained and less stiff in regions where growth is to be permitted.

Figure 1B:
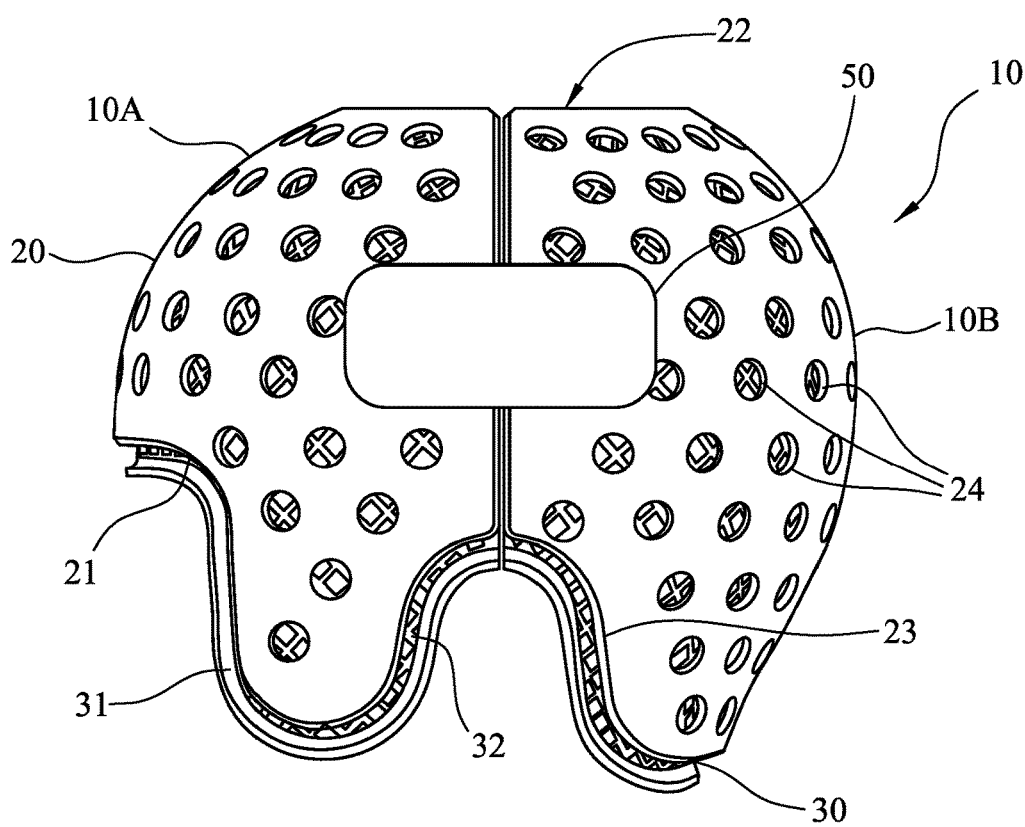
Figure 1C:
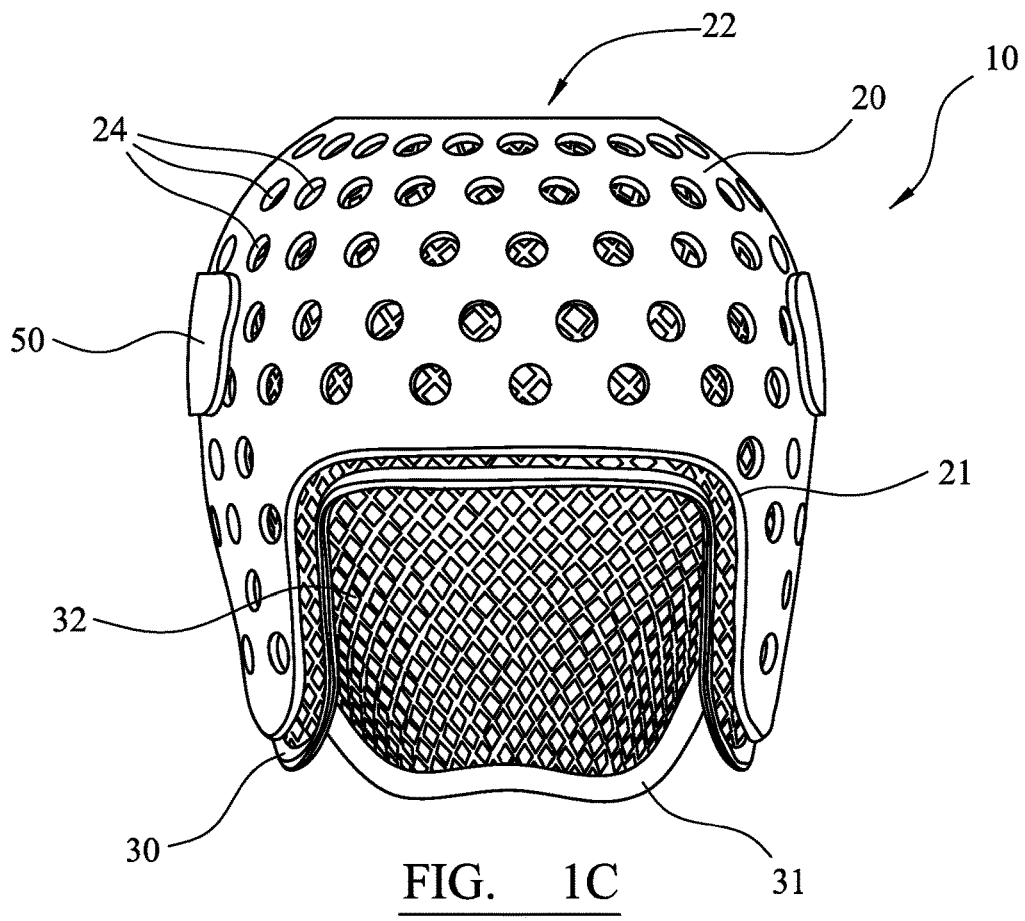

FIGS. 1A-1C show an orthosis 10 in accordance with an embodiment of the invention. The orthosis 10 is shaped to surround a substantial portion of the head of a wearer, and effectively takes the form of a helmet. The orthosis 10 comprises an outer layer 20 and a mesh layer 30.

Figure 2:
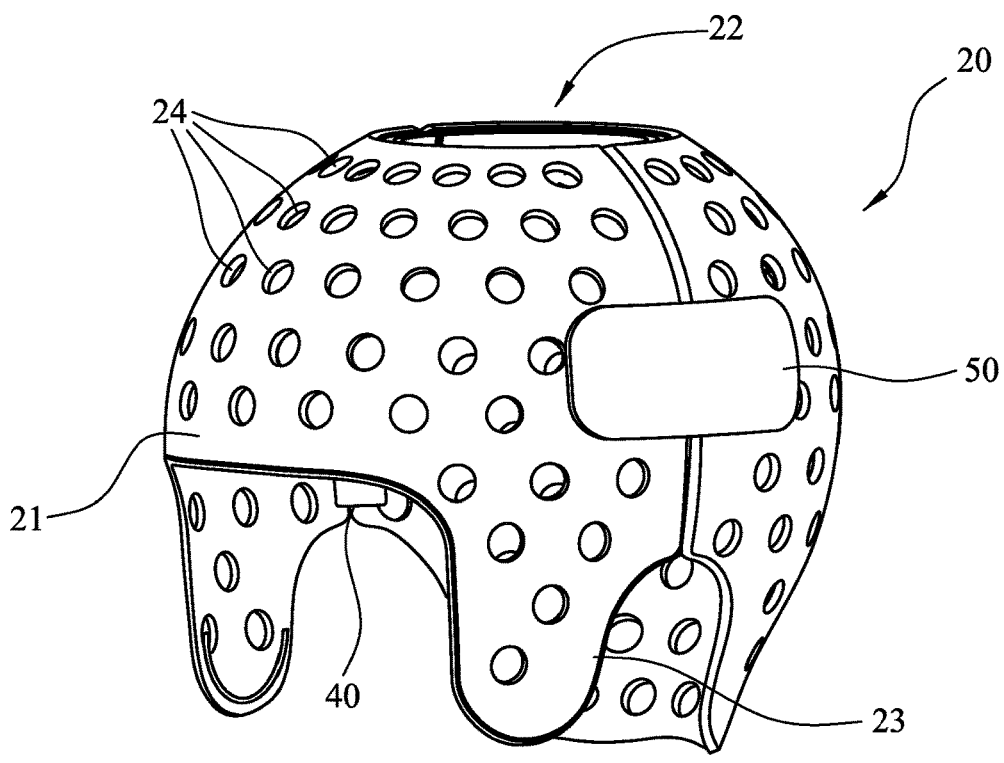
FIG. 2 is a perspective view of an outer shell of the orthosis.

The outer layer 20, shown separately in FIG. 2, defines the exterior shape of the orthosis 10. The outer layer 20 is substantially rigid, thereby supporting the other elements of the orthosis 10, as well as providing protection to the head of the wearer. The orthosis 10 extends to meet the neck of the wearer at the rear of the head. Recesses 21 and 23 are provided in the outer layer 20 to respectively accommodate the face and ears of the wearer.

An aperture 22 is provided in the top surface of the orthosis 10, so as to provide ventilation to the top of the wearer's head. A plurality of further, smaller ventilation apertures 24 are provided in the surface of the outer layer 20. In one example, the smaller ventilation apertures 24 are approximately 1 mm to 15 mm in size. In one example, the ventilation apertures 24 are disposed relatively uniformly around the orthosis 10, so as to provide good ventilation to a substantial portion of the wearer's head in use. The ventilation apertures 24 may also form part of the external decoration of the shell, In further examples, the ventilation apertures 24 are provided in channels, or partially covered by 3D projections.

The outer layer 20 is manufactured from a stable semi rigid plastic material. In the example shown, the outer layer 20 comprises a single layer. However, in further examples, the outer layer 20 may comprise multiple layers, for example two layers.

Figure 3:
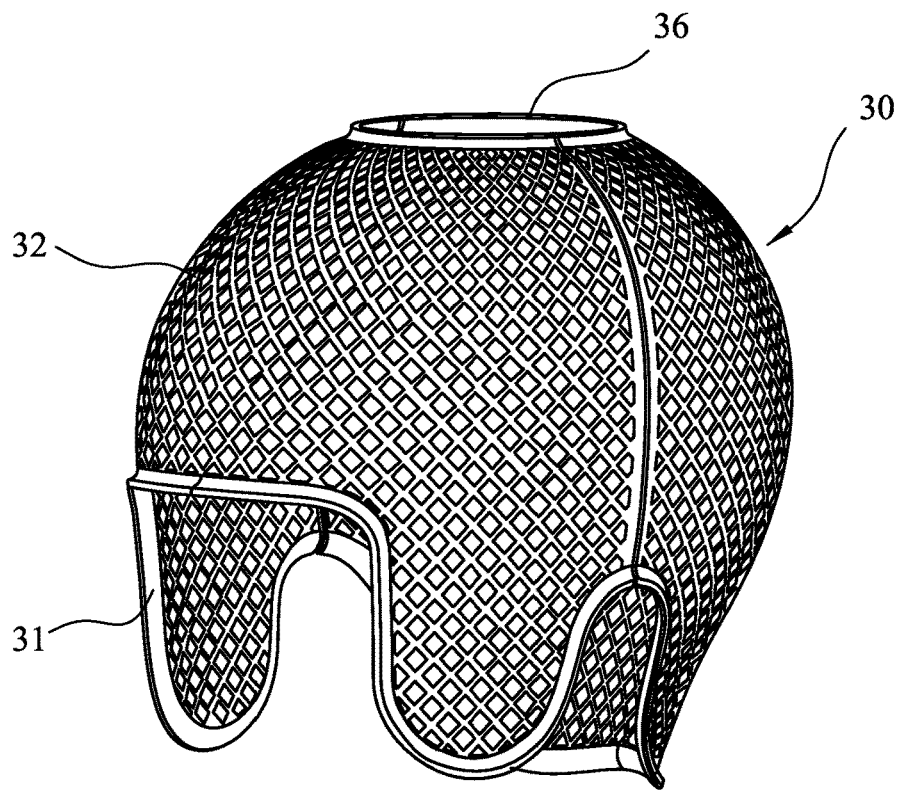
FIG. 3 is a perspective view of a mesh layer of the orthosis.

The mesh layer 30, shown separately in FIG. 3, is disposed substantially within the outer layer 20, and corresponds substantially in shape to the outer layer. In one example, a portion of the mesh layer 30 may extend beyond the edges of the outer layer 20. In one example, the mesh layer 30 comprises an aperture 36 at a position corresponding to the aperture 22 of the outer layer 20.

Figure 5A:
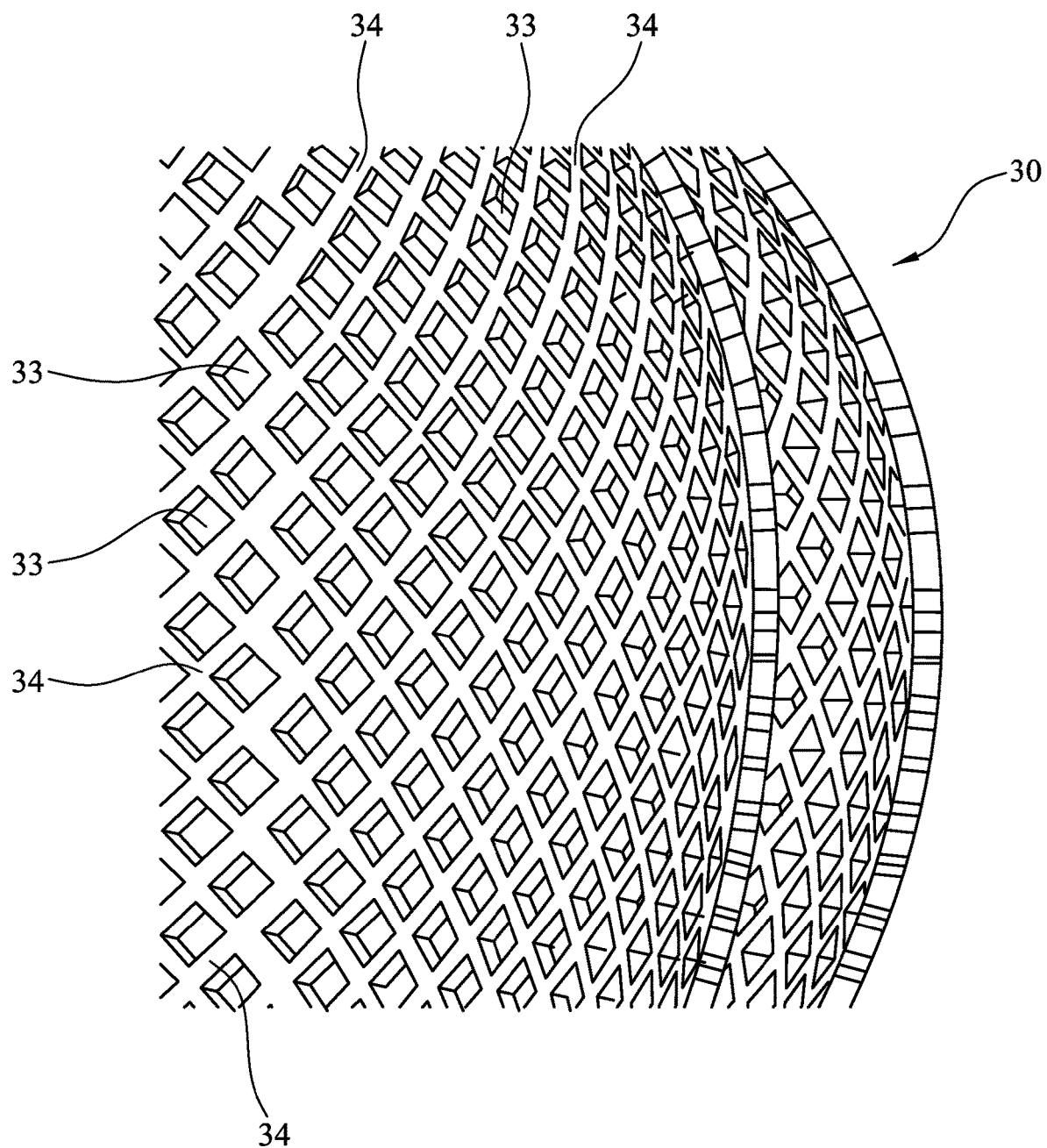
FIG. 5A is an enlarged view of a portion of the mesh layer of FIGS. 3 and 4.

The mesh layer 30 substantially comprises a variably flexible mesh 32. The mesh 32 is disposed within a border 31. The mesh 32 comprises a large number of relatively small apertures 33 formed in the body of the mesh layer 30. In one example, the apertures 33 are defined by members 34 (best seen in FIG. 5A). In one example, the members 34 are substantially diagonal, and therefore define diamond shaped apertures 33. It will be understood, however, that various patterns of mesh structure could be employed, defining various shapes of aperture.

Figure 5B:
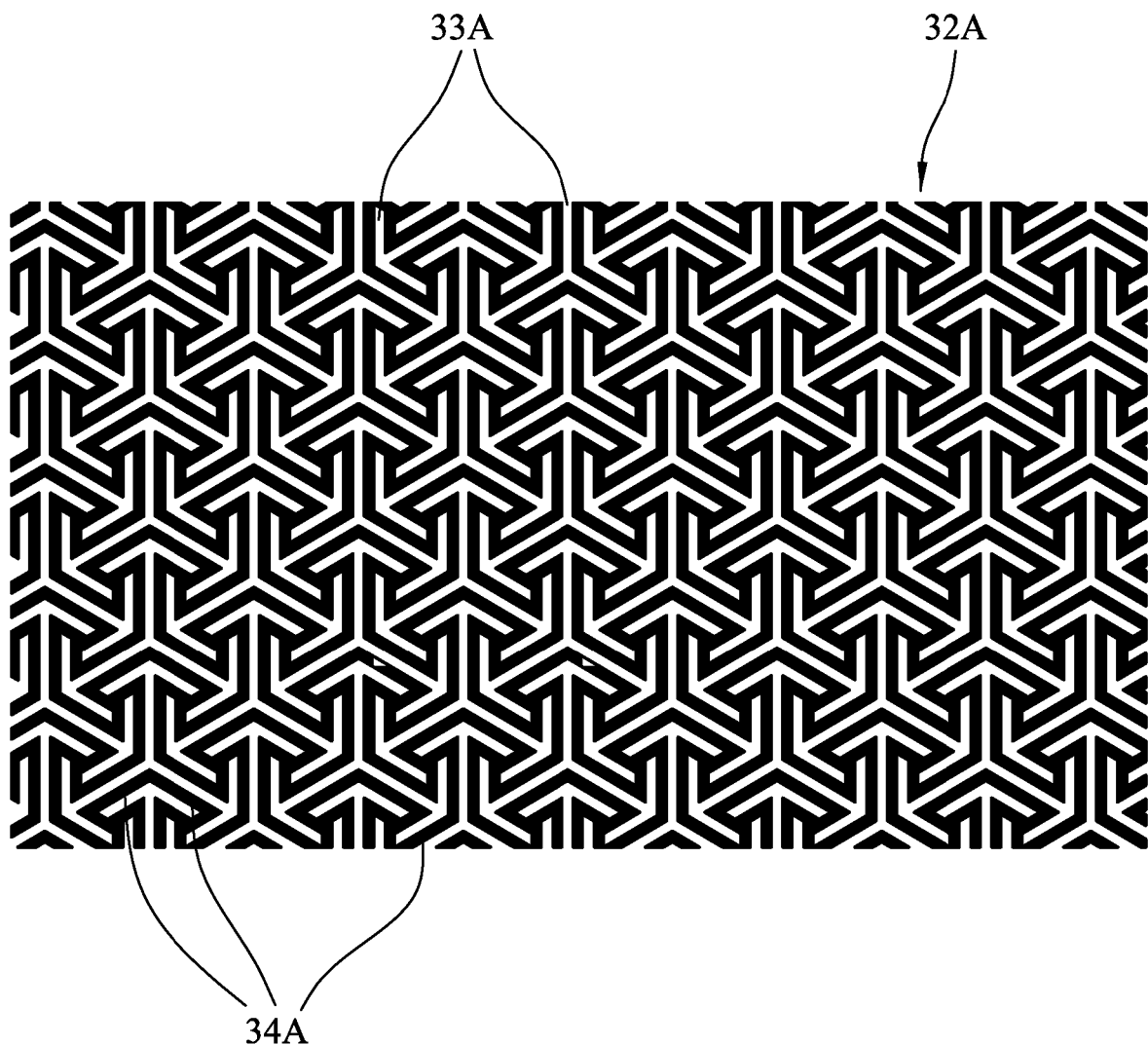
FIG. 5B is a view of a mesh layer of the orthosis according to an embodiment of the invention.

FIG. 5B shows a mesh 32A according to a further example. The mesh 32A comprises members 34A and apertures 33A, which define an auxetic structure. The auxetic structure has a negative Poisson's ratio, so that the structure becomes thicker perpendicular to the direction of a force applied to the structure. Whilst the mesh 32A shows a pattern that is defined in two dimensions, it will be understood that the auxetic structures could also be three dimensional in structure.

The flexibility of the mesh 32 varies according to the form and density of the mesh—i.e. the size and concentration of the apertures 33 and in comparison to the material of the body of the mesh layer 30. If the members 34, which form rib structures either in two or three dimensions, are stronger or thicker in a region of the mesh 32, that region is less flexible (i.e. stiffer). Conversely, if more and/or larger apertures 33 are present in a region of the mesh 32 (thereby looking more 'stretched' or 'open'), less of the material forming the members 34 is present in that region and therefore the region is more flexible. Additionally or alternatively, the flexibility of the mesh 32 can be varied by forming the members 34 from material that is inherently more or less flexible. In other words, a region of the mesh 32 that is less flexible may be formed from a less flexible material, and a region of the mesh 32 that is more flexible may be formed from a more flexible material. Accordingly, areas of varying density and flexibility can be provided in the mesh 32, so as to constrain growth of the wearer's skull in some regions, whilst allowing growth in other regions. The apertures 33 also provide ventilation to the wearer's head.

Although the meshes 32, 32A comprise a relatively uniform repeating structure of apertures 33 and members 34, varying flexibility can also be provided by varying the structure of the mesh. For example, a more flexible region of the mesh may have a first structure or pattern, and a stiffer portion of the mesh may have a second, different structure or pattern.

The mesh layer 30 is manufactured from rigid, semi rigid or flexible plastic material.

Figure 4:
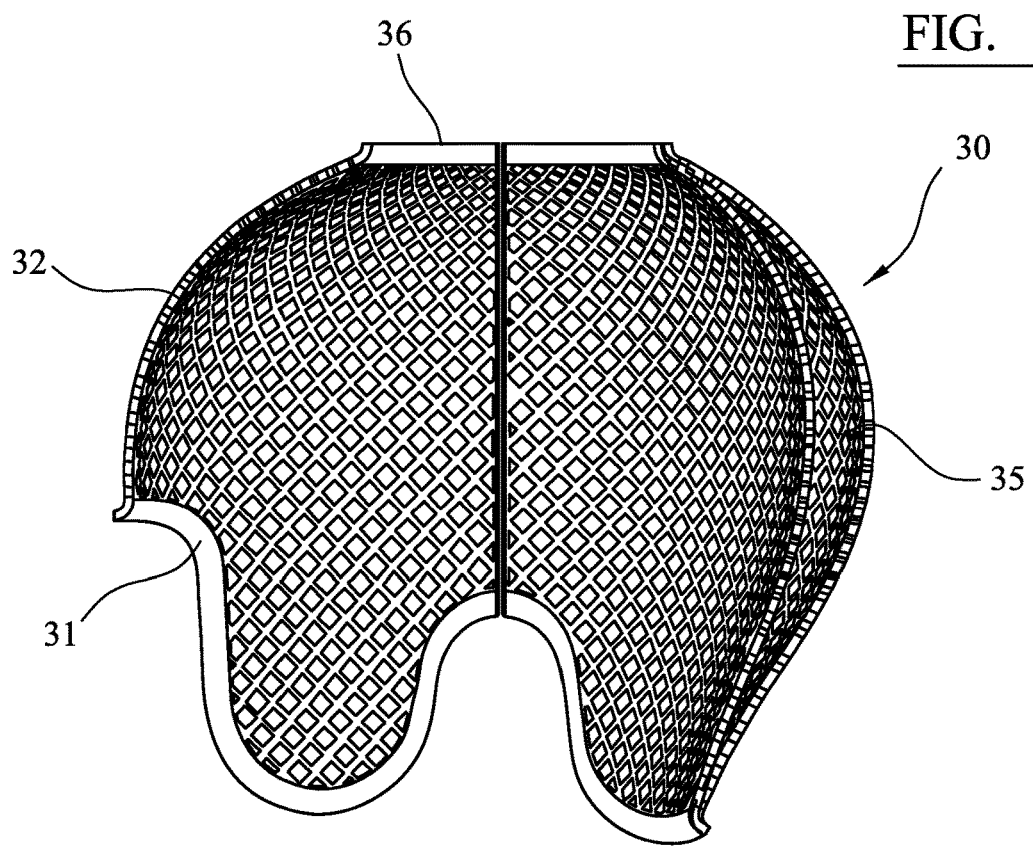
FIG. 4 is a side view of a mesh layer of the orthosis.

It will be understood that the shape of the mesh layer 30, and the outer layer 20, will be varied according to both the current and desired head shape of the wearer. FIG. 4 shows an example of the mesh layer 30, in which there is a region 35, which defines a void between the mesh layer 30 and the outer layer 20, so as to accommodate growth in the wearer's head.

In one example, the orthosis is arranged such that the outer layer 20 and mesh layer 30 are separated by a gap. For example, the gap between the layers may be from approximately 0 mm to 30 mm. Accordingly, force applied to the outer layer 20, such as from accidental contact with hard surfaces, does not cause deformation of the mesh layer 30.

The orthosis 10 further comprises a closure means. The closure means allows the orthosis 10 to be adequately secured to the wearer's head in a first configuration, and to be sufficiently loose to enable to the easy removal and fitting of the orthosis 10 in a second configuration.

In one example, the orthosis 10 is divided by a vertical plane into two portions 10A, 10B (see FIG. 1B). In this example, the closure means comprises a hinging portion 40 and a fastening means 50. The hinging portion 40 is disposed substantially vertically on one side of the orthosis, and hingedly connects the two portions 10A, 10B. The hinging portion 40 comprises a hinge disposed on the outer layer 20. In one example, the hinging portion 40 also comprises a hinge disposed on the mesh layer 30 at a corresponding position to the hinge disposed on the outer layer 20. In one example, at least one of the hinges is a living hinge that is formed from the same material as the two portions of the layer it connects. The hinging portion 40 enables the orthosis 10 to open and close. The position of the opening and the top of the hinge can be varied to enable variable compression on differing parts of the wearer's skull. The fastening means 50 acts to secure the orthosis 10 in the first configuration when engaged. The fastening means 50 may comprise any suitable engagable means of securing the orthosis 10 in position, including any suitable latch mechanisms, adhesive materials and so on.

In one example, the outer layer 20 and the mesh layer 30 are secured together by means of monobloc design, wherein both parts are additively manufactured simultaneously. In further examples, the layers are secured together by hook and loop fastener material, such as Velcro®, click locked together, or secured using pin and hole type fastenings.

Figure 6A:
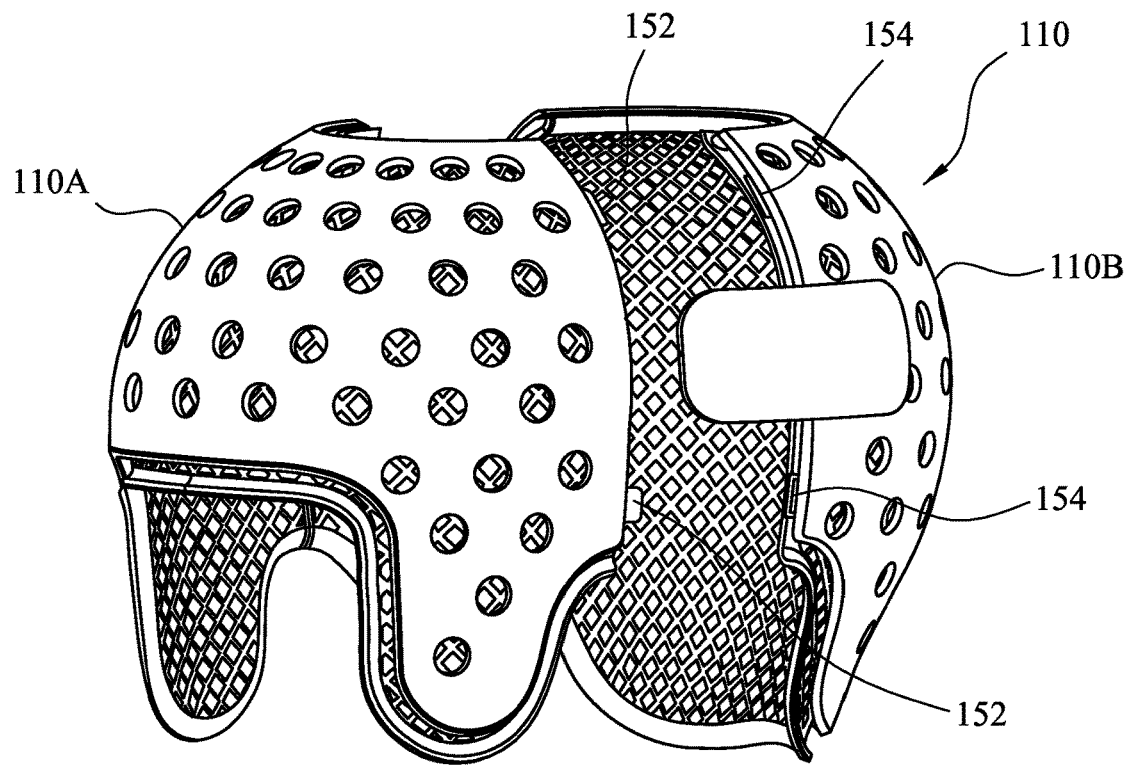
FIGS. 6A and 6B are respectively partially-exploded perspective and side views of the orthosis.
Figure 6B:
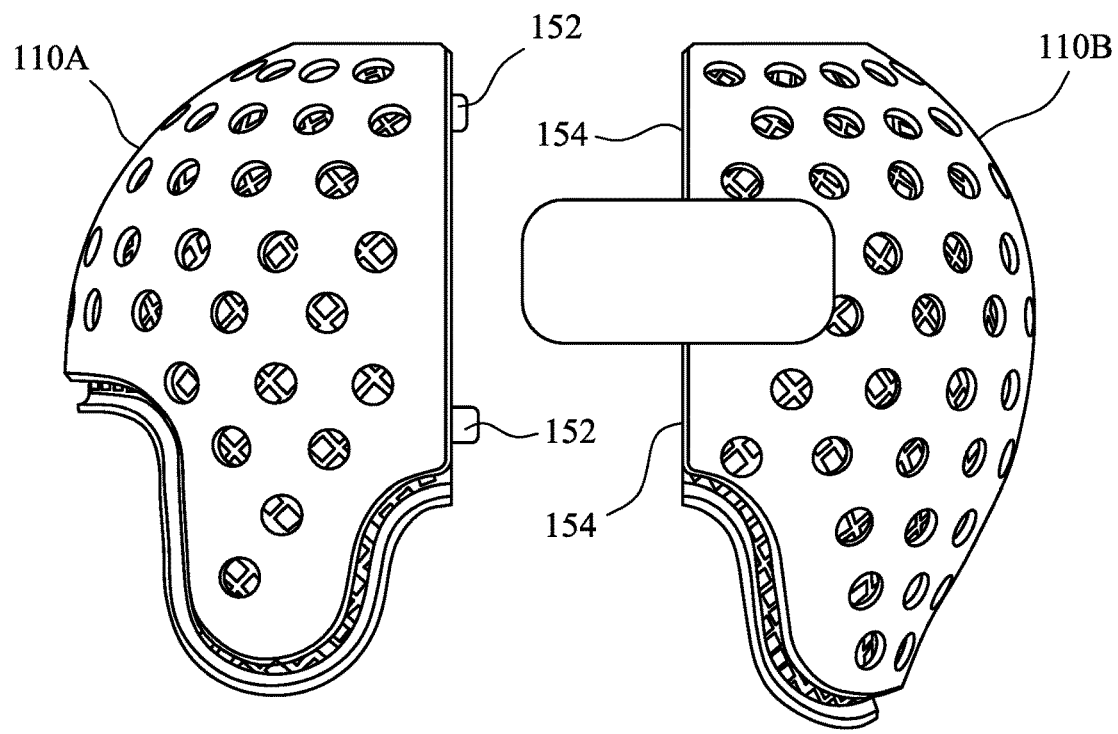

FIGS. 6A and 6B illustrate an orthosis 110 comprising alternative closure means. The orthosis 110 also comprises two vertically divided portions 110A, 110B. Rather than being hingedly connected, the orthosis 110 instead separates into the two portions for removal. In one example, tabs 152 and corresponding slots 154 are provided to aid locating the two portions 110A, 110B with respect to each other during fitting. The tabs 152 and slots 154 also serve to impart circumferential strength to the outer layer. It will be understood that the tabs 152 and slots 154 may also be employed in hingedly connected examples of the invention, to aid repeatable location of the hinged portions.

Figure 7:
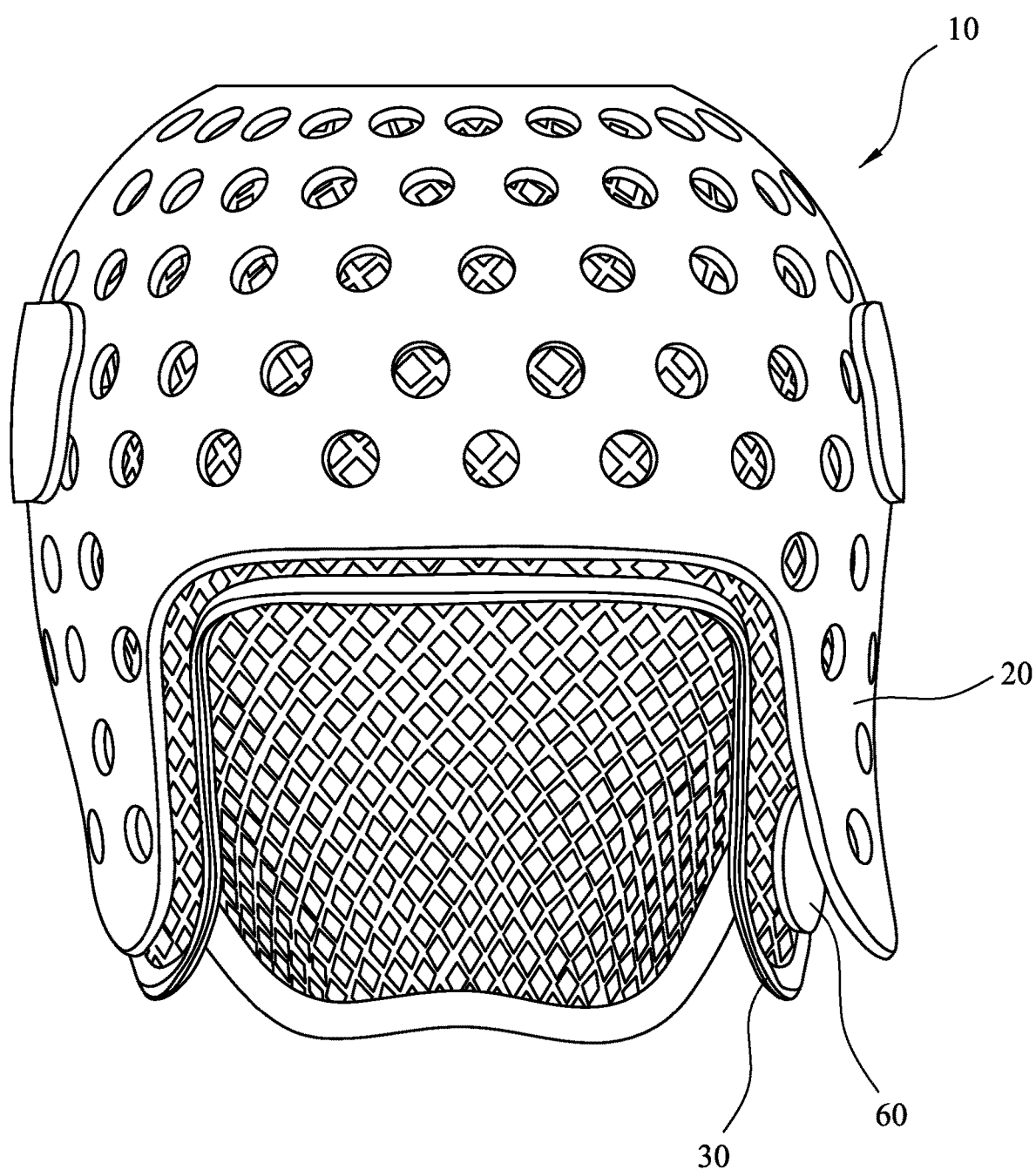
FIG. 7 is a front view of an orthosis according to an embodiment of the invention.
Figure 8:
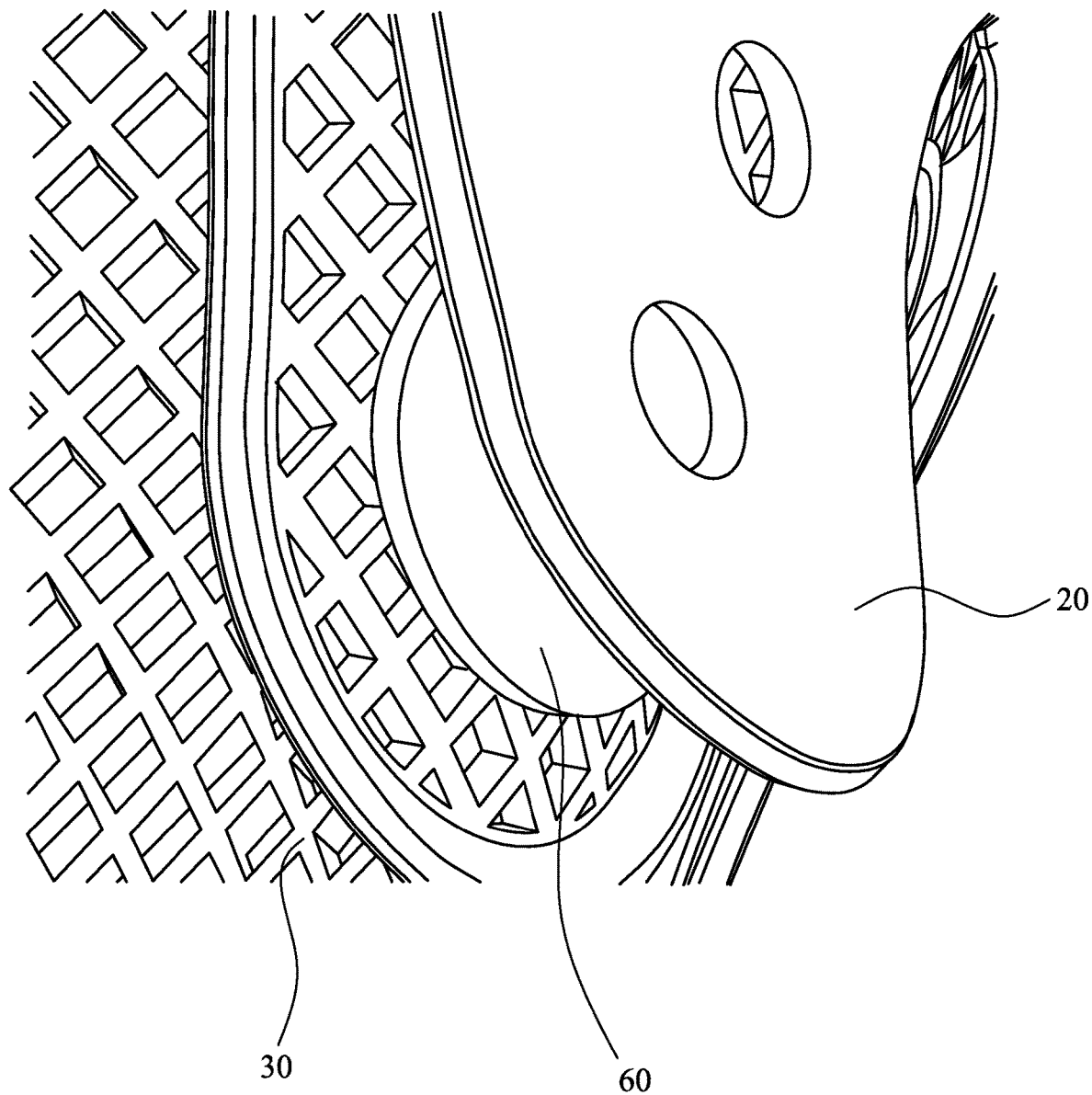
FIG. 8 is an enlarged view of a portion of the orthosis of FIG. 7.

Referring to FIGS. 7 and 8, in one example the orthosis 10 further comprises pads 60. The pads are disposed between the outer shell 20 and mesh layer 30. One or more pads 60 may be fitted to adjust the flexibility of a region of the orthosis 10 and/or to adjust the shape and volume of the orthosis 10 to optimize the effect thereof. The pad 60 also serves to prevent the orthosis 10 rotating on the wearer's head.

Figure 17:
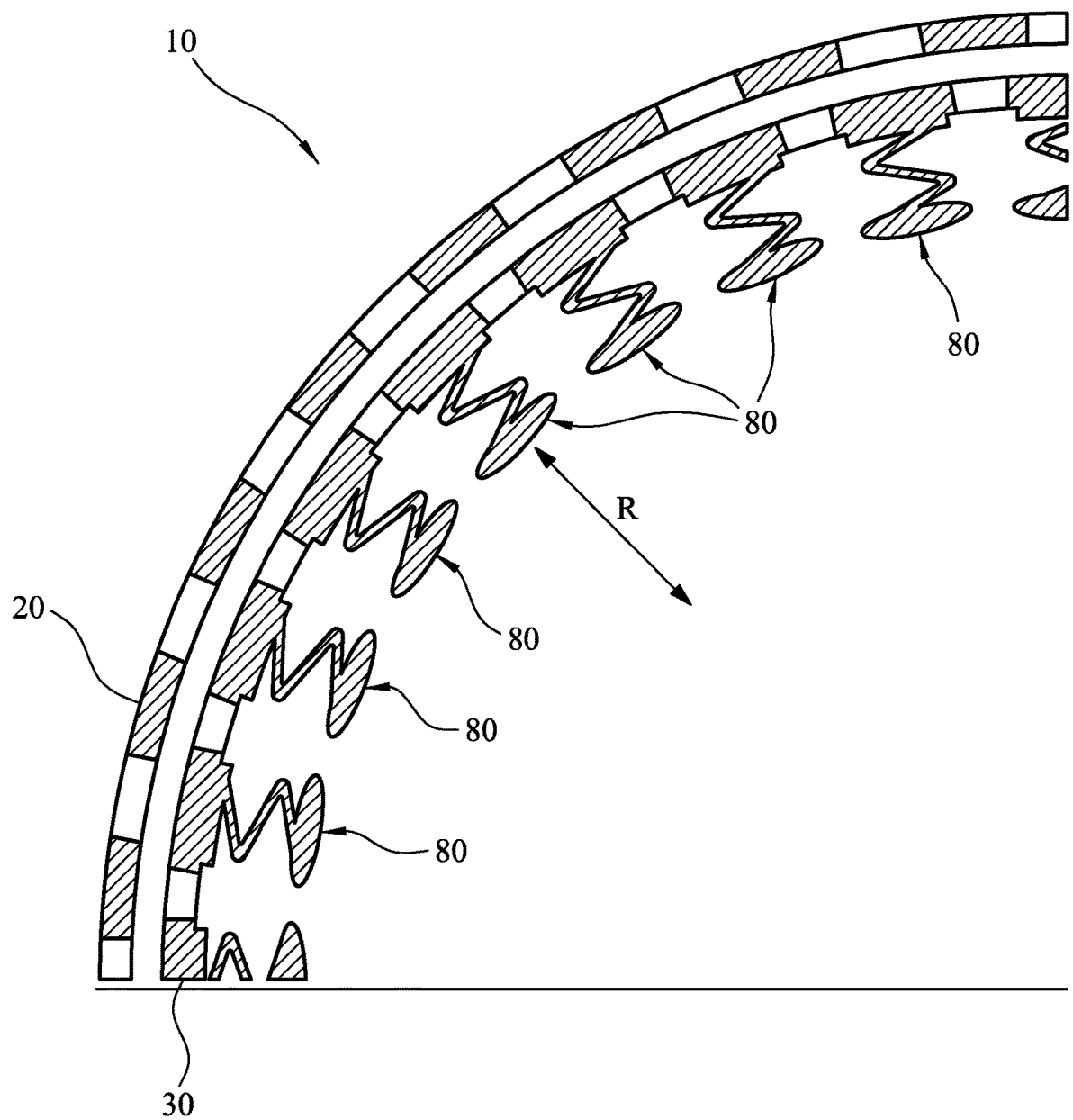
FIG. 17 is a cross-section of an orthosis according to an embodiment of the invention.

FIG. 17 shows a further example orthosis 10 in cross-section. The orthosis 10 comprises a plurality of cushioning elements 80, which are resiliently deformable elements that act to provide cushioning to the wearer and improve the fit of the orthosis 10 without exceeding capillary pressure at any one point on the wearer's head. The cushioning elements 80 are resiliently deformable substantially in a radial direction R with respect to the wearer's head.

In the example shown in FIG. 17, the cushioning elements 80 are disposed on the interior surface of the mesh layer 30. Particularly, the cushioning elements 80 are distributed regularly over the interior surface of the mesh layer 30. In further examples, the cushioning elements are positioned in between the outer layer 20 and mesh layer 30, for example by being distributed over the surface of the outer layer 20. In one example, the cushioning elements 80 are be formed integrally with either the mesh layer 30 or the outer layer 20. In further examples, the cushioning elements 80 are formed separately and then subsequently attached to the relevant layer 20, 30.

Figure 18:
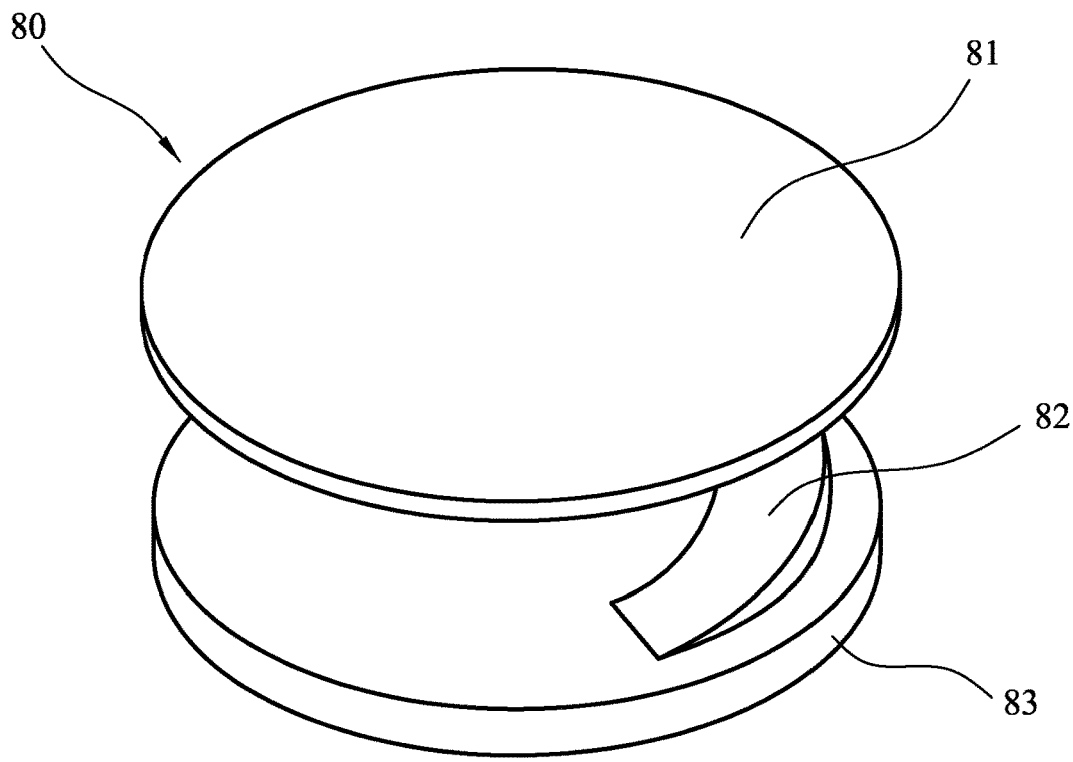
FIGS. 18, 19 and 20 are respectively an upper perspective, lower perspective and side view of one of the cushioning elements shown in FIG. 17.
Figure 19:
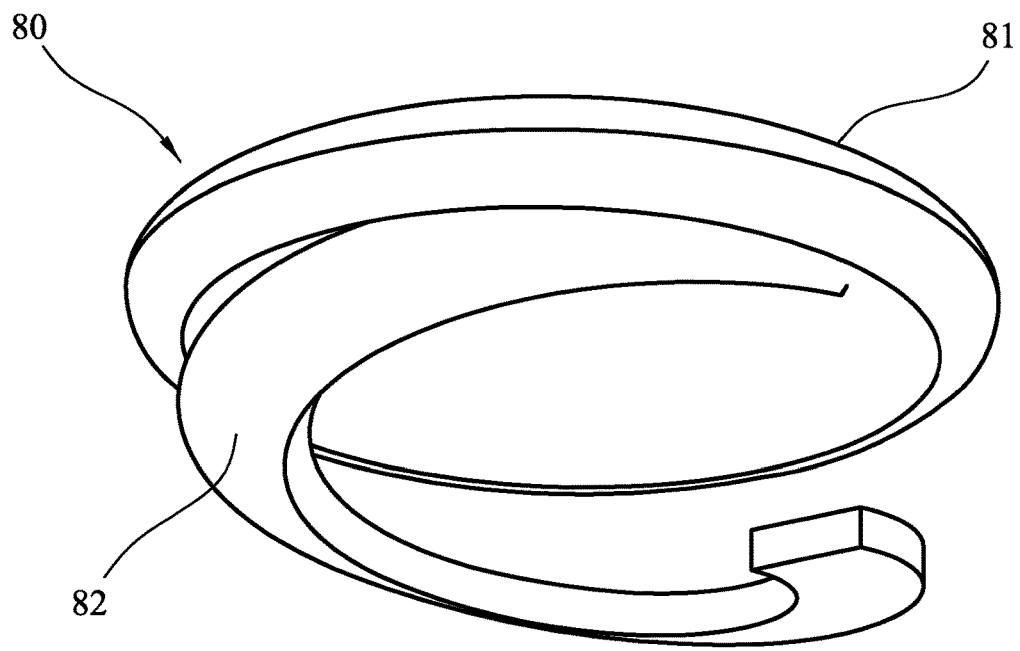
Figure 20:
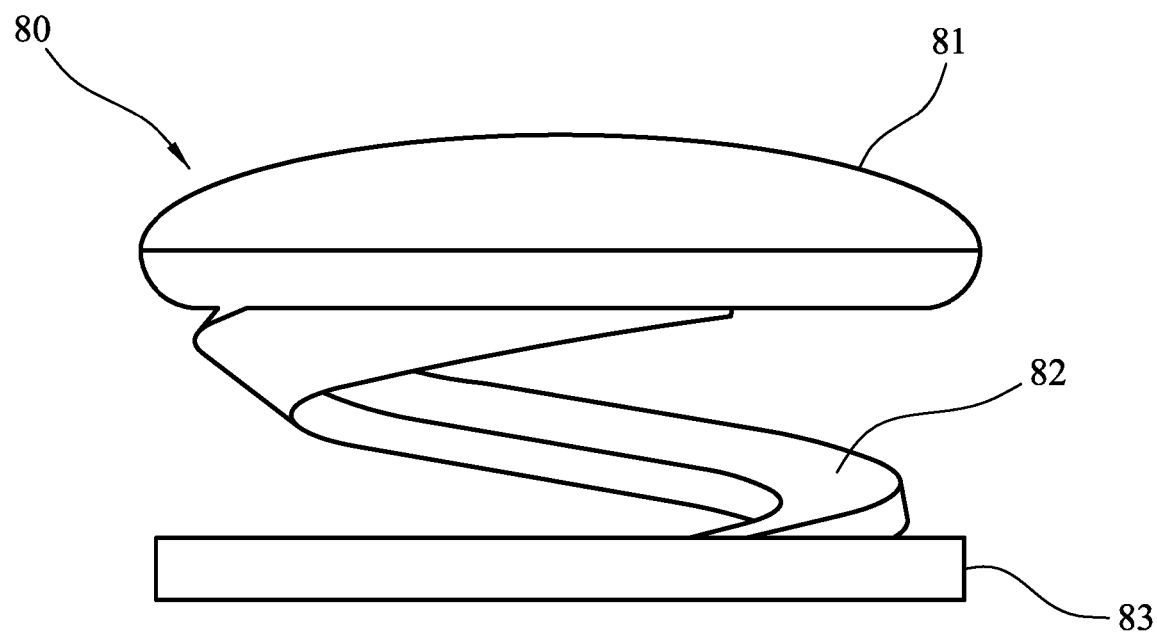

The cushioning elements 80 are shown in more detail in FIGS. 18-20, and comprise a cushion portion 81, a spring portion 82 and a base portion 83. The base portion 83 is attached to the mesh layer 30 or outer layer 20, or in examples where the cushioning elements 80 are integrally formed with a layer, form part of the layer. The spring portion 82 extends between from the base portion 83 and the cushion portion 81, and is flexible so as to be resiliently deformable. In one example, the spring portion 82 is a helical spring. The cushion portion 81 is a dome-shaped member, adapted to receive pressure exerted by movement of the wearer's head, either by directly contacting the wearer's head, or by contacting a layer (e.g. mesh layer 30) that is deformable.

Figure 9:
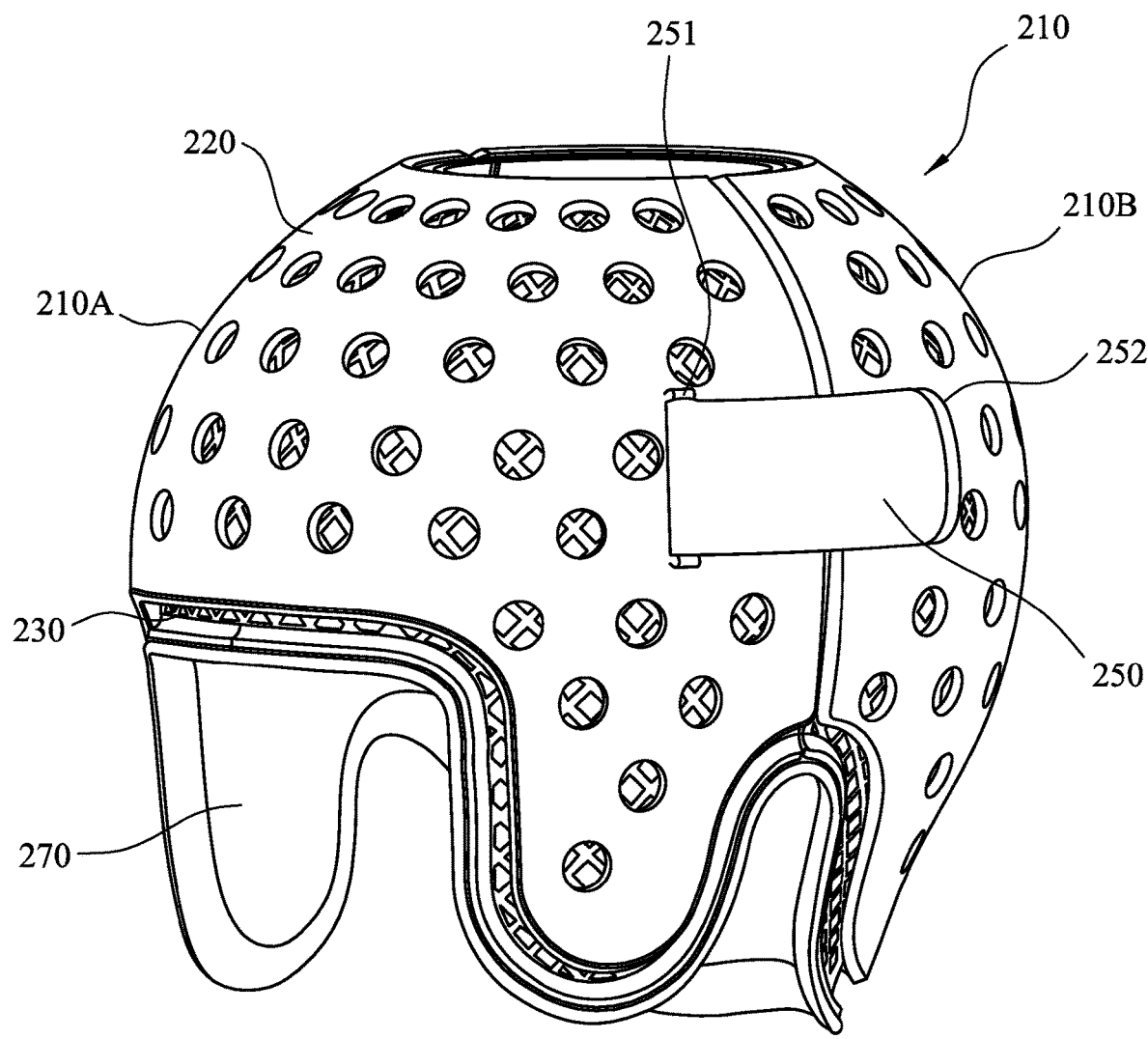
FIG. 9 is a perspective view of an orthosis according to an embodiment of the invention.

FIG. 9 shows an orthosis 210 in accordance with a further embodiment of the invention. The orthosis 210 comprises an outer layer 220, a mesh layer 230 and a liner 270. The outer layer 220 and mesh layer 230 are substantially as described above with reference to orthosis 10, and therefore the description thereof will not be repeated.

Figure 10:
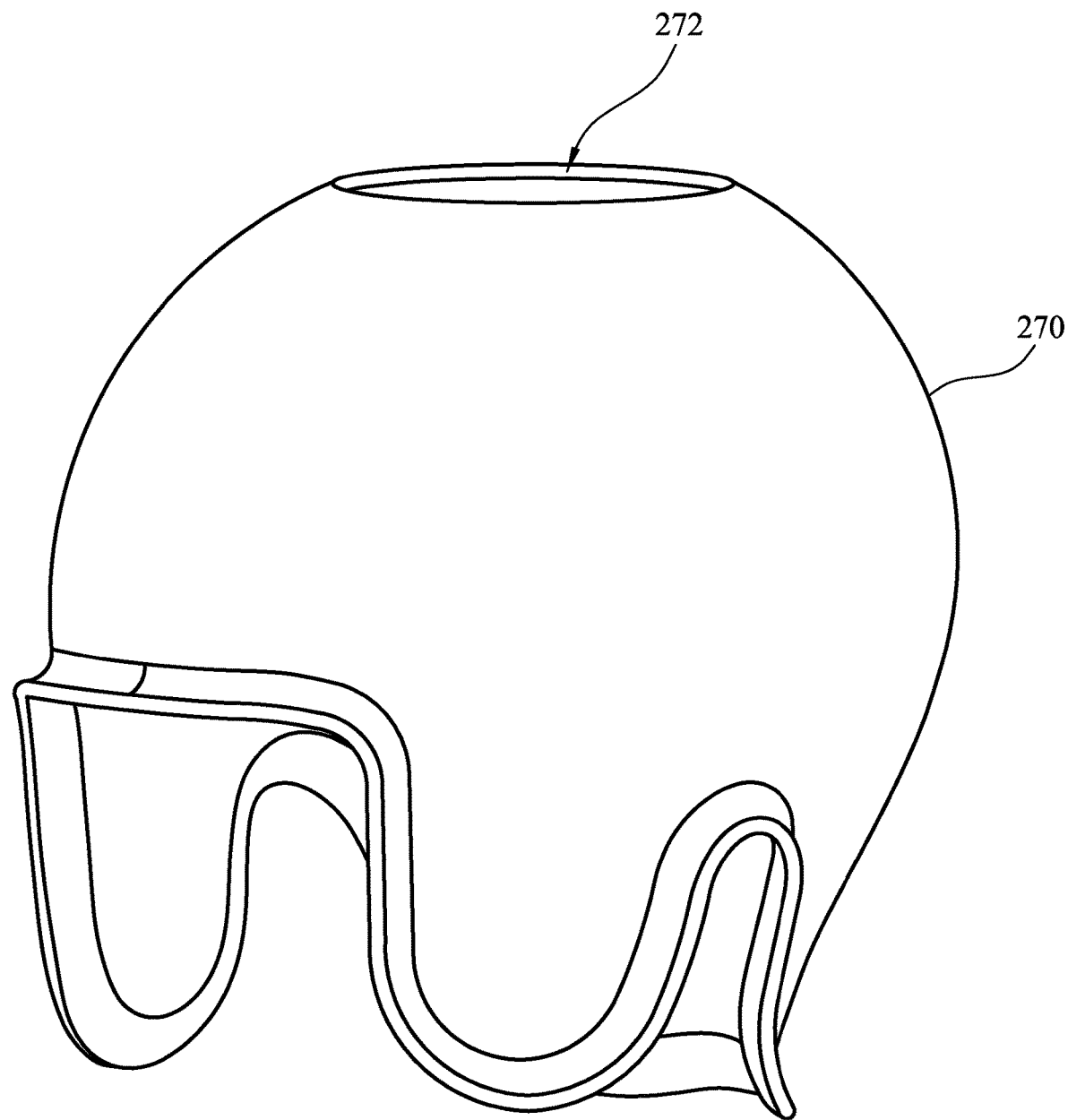
FIG. 10 is a perspective view of the liner layer of the orthosis of FIG. 9.

The liner 270, seen separately in FIG. 10, is disposed substantially within the mesh layer 230, and corresponds substantially in shape with the mesh layer 230. The liner 270 primarily serves to increase the comfort to the wearer by providing padding. The liner 270 also acts to prevent rotation of the orthosis 210 on the wearer's head.

The liner 270 comprises a material that is breathable, thereby ensuring ventilation for the wearer's head. The liner 270 is also self-wicking, transferring moisture away from the wearer's head due to capillary action.

In one example, the liner 270 is attachable and detachable from the orthosis 210. This allows the liner 270 to be cleaned or replaced periodically. In one example, the liner 270 is formed of a washable material, so that it can be removed and washed.

In one example, the liner 270 is attached to the orthosis 210 by a suitable attachment means (not shown), such as a hook and loop fastener, internally fixed fastenings or locators, externally fixed fastenings or the like. In a further example, the shape of the liner 270 ensures that it is retained within the orthosis 210 without the need for specific attachment means. Particularly, the liner 270 is resiliently deformable such that it is pushed into the orthosis 210 and then is biased to return to a shape in which it is securely retained within the orthosis 210.

In one example, the liner 270 comprises an aperture 272 at a position corresponding to the apertures 22 and 36 of the outer layer and mesh layer respectively.

Figure 11A:
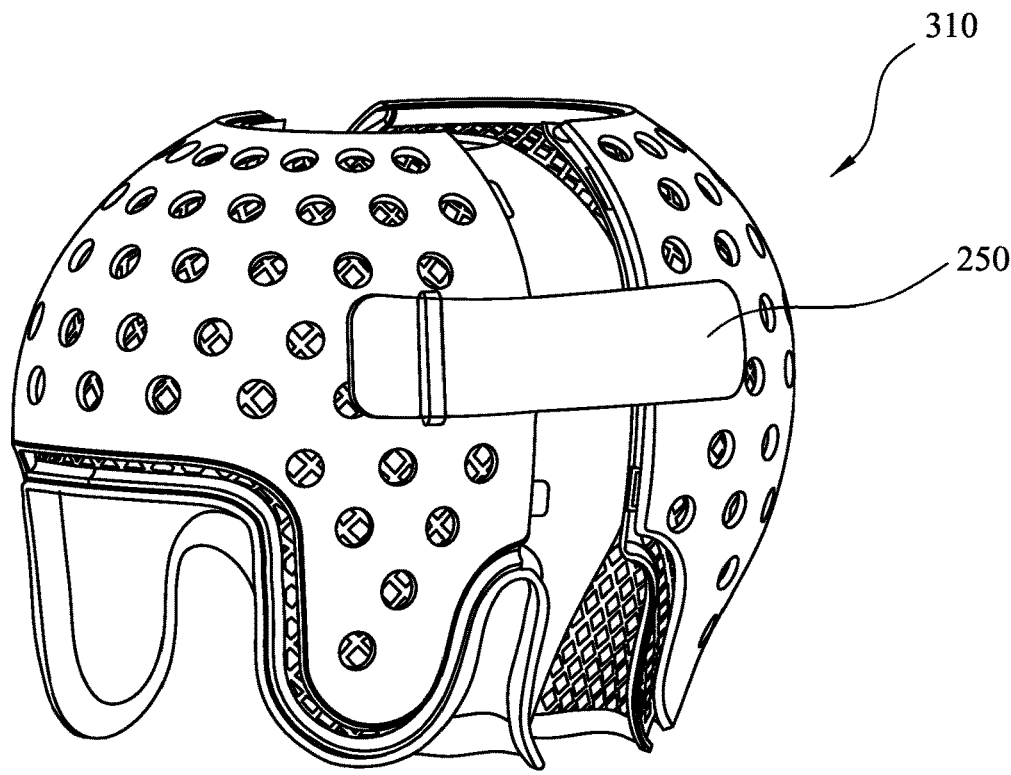
FIGS. 11A and 11B are respectively a perspective view and a side view of a closure means of the orthosis of FIG. 9.
Figure 11B:
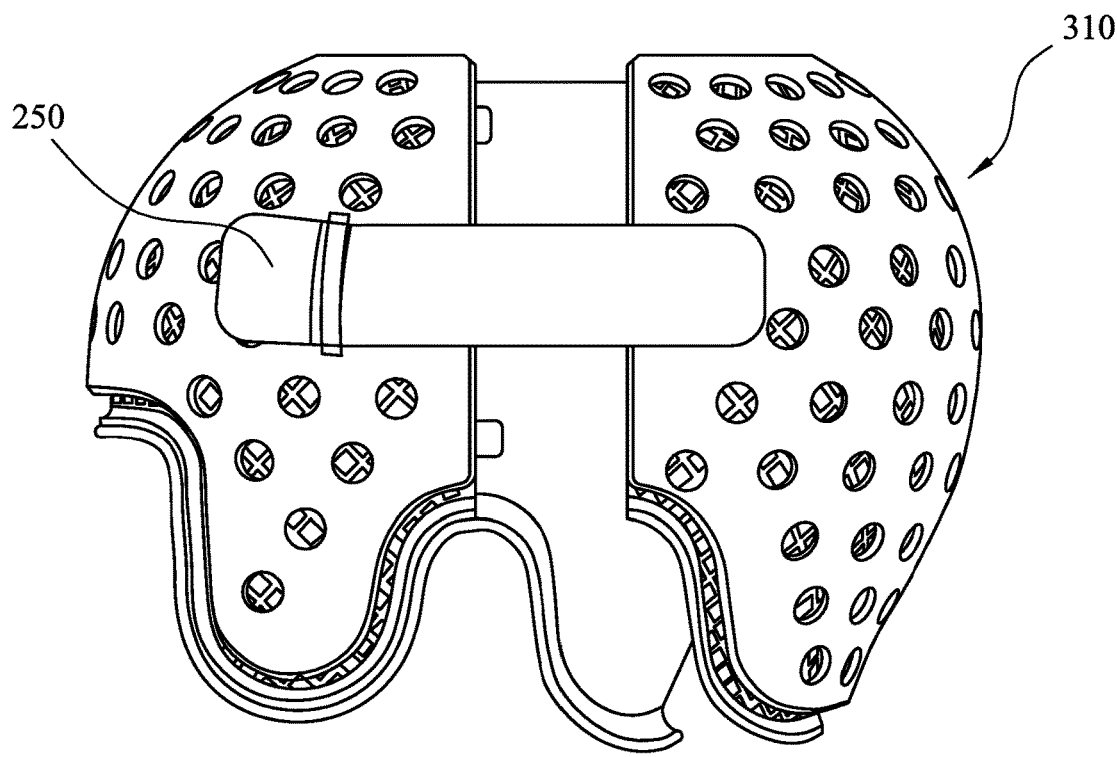

The orthosis 210 comprises an alternative fastening means 250. The fastening means 250 comprises a length of hook and loop fastener material 252, such as Velcro®, and a looping portion 251. The length of hook and loop fastener material 252 is affixed to one of the vertically divided portions 210B, and the looping portion 251 is disposed on the other portion 210A. The portions 210A,B are secured in the first configuration by passing a part of the length of hook and loop fastener 252 through the looping portion 251, and then folding that part of the hook and loop fastener 252 over so that it is secured to itself. As can be seen in FIGS. 11A and 11B, this fastening means 250 may also be employed in an orthosis 310 separable into two portions, rather than being hingedly attached.

Figure 12:
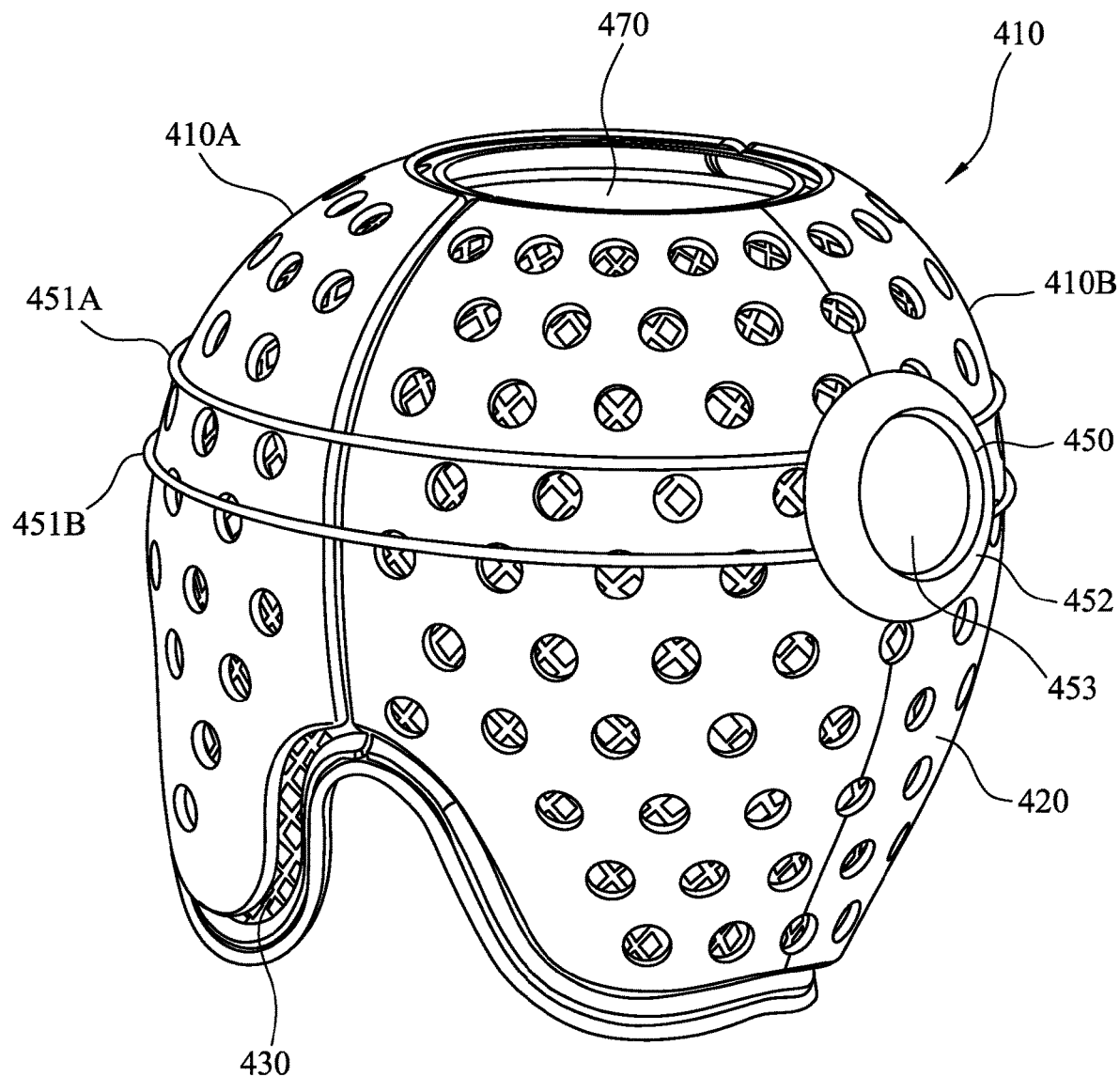
FIG. 12 is a perspective view of an orthosis according to an embodiment of the invention.

FIG. 12 shows an orthosis 410 according to a further embodiment of the invention. The orthosis 410 comprises an outer layer 420, a mesh layer 430 and a liner 470 as described above with reference to the other embodiments of the invention.

The orthosis 410 further comprises two hingedly connected portions 410A, 410B, and a fastening means 450. The fastening means comprises two wires or cables 451A, 451B, which are disposed substantially horizontally around the circumference of the orthosis 410, and a tightening means 452. The tightening means 452 tightens the wires 451A, 451B when rotated in one direction, thereby securing the orthosis 410 in the first configuration. The tightening means 452 is also configured to loosen the wires, for example by pressing a button 453, or rotating the tightening means 452 in the opposite direction, thereby loosening the orthosis 410.

It will be understood that the closure means described herein are substitutable and interchangeable. It will be further understood that, whilst the orthoses described herein substantially surrounds the head of the wearer, the othoses may only surround a portion of the head of the wearer.

In use, the orthosis 10 is loosened to the second configuration using the closure means, and then placed over the head of the wearer. The orthosis 10 is then tightened to the first configuration. Accordingly, suitable pressure is applied to the head of the infant by the orthosis 10 to correct the head shape of the infant.

Figure 13:
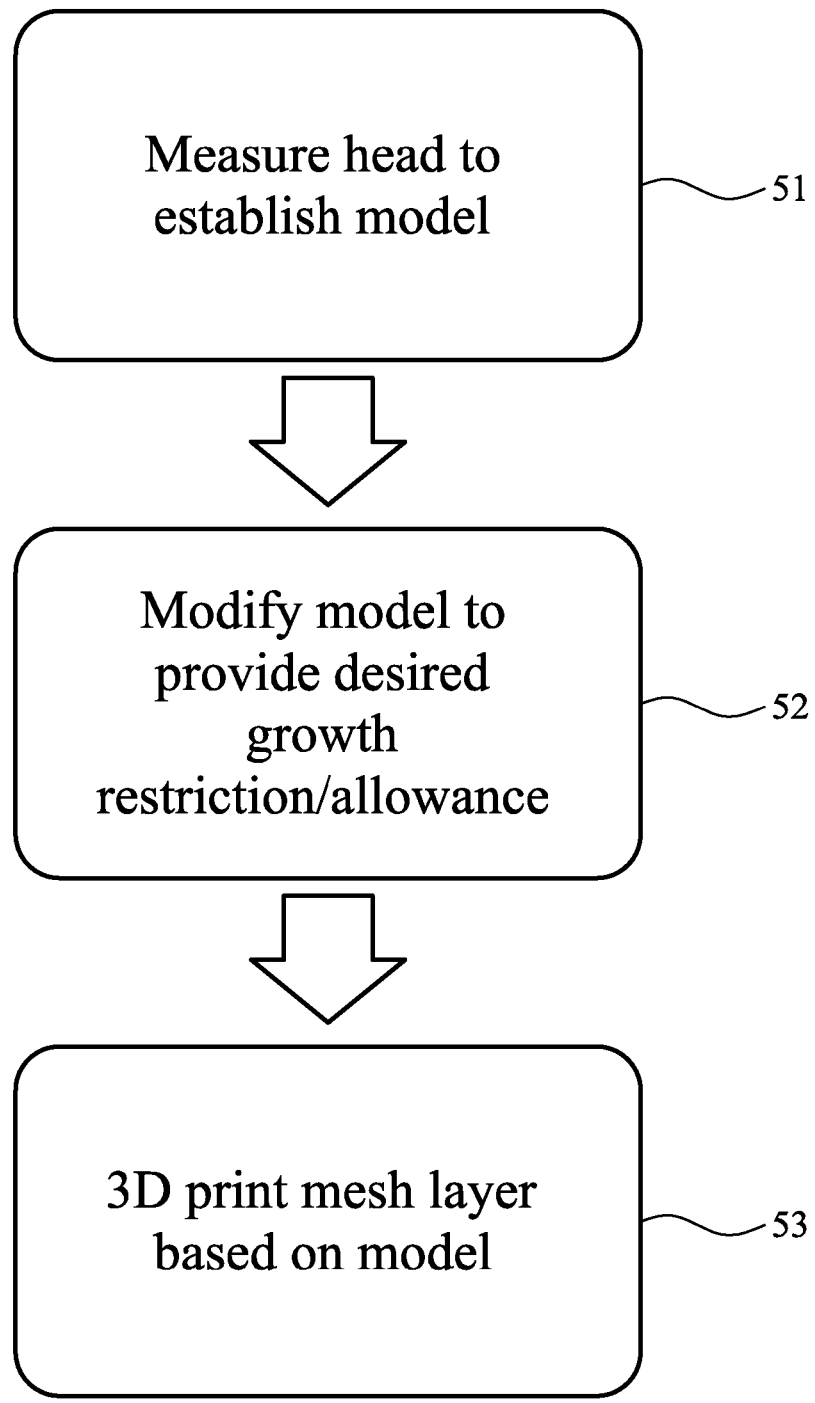
FIG. 13 is a flowchart of a method of manufacturing an orthosis.

A method of manufacturing an orthosis 10 will now be described, with reference to FIG. 13.

Firstly, in step 51, the head of the wearer is measured to establish a virtual 3D model of the head. In one example, a 3D scan is taken of the infant's head, and a 3D point cloud is established that represents the shape of the wearer's head in 3D space. The scanning process may be aided by attaching reference point location markers to the head. In one example, a sock is placed over the head, with stick-on location markers affixed thereto.

In other examples, an MRI scan, a CT scan, a plurality of 2D or 3D images, or manual measurements can be used to establish the 3D model.

Secondly, in step 52, the 3D model of the head is modified to so that the shape includes regions where growth is allowed or growth is restricted. This is typically done in suitable computer-aided design software, by a suitably trained user with the knowledge to assess what shape will correct the deformity. In some examples, the model is modified by the application of predefined routines or protocols that provide a commonly required modification to the model. In some examples, the user compares the model to a library of suitable shapes i.e. standard shapes for correcting particular deformities, and modifies the model with reference to a suitable library shape. In some examples, the user makes freehand modifications to the model, based on their assessment of the shape of the deformities and the required shape of the orthosis.

Thirdly, in step 53, the mesh layer 30 of the orthosis 10 is formed based on the model, using a 3D printer or other suitable additive manufacturing means. In one example, the 3D printer makes use of a material that is suitable for prolonged contact with the skin of the wearer without irritation. Accordingly, a mesh layer 30 suitable for the particular needs of an individual wearer can be easily manufactured.

In one example, the outer layer 20 is formed separately, and the mesh layer 30 is then subsequently affixed within the outer layer 20. In one example, the outer layer 20 is also formed using a 3D printer or other suitable additive manufacturing means. This allows the dimensions of the outer layer 20 to be easily customised based on the head shape of the user. In a further example, the outer layer 20 is formed using injection moulding or plastic thermoforming. This allows for cost-effective production of the outer layer 20 in one or more standard sizes, with only the mesh layer 30 being specifically adapted for the wearer's head.

The mesh layer 30 is then inserted into the outer layer 20 and the two layers are secured together. In one example, the layers are secured together by hook and loop fastener material, such as Velcro®, click locked together, or secured using pin and hole type fastenings.

In a further example, the outer layer 20 and the mesh layer 30 are formed concurrently or simultaneously. In such an example, the layers are secured together by means of a monobloc design. Particularly, the outer layer 20 and the mesh layer 30 are printed concurrently in a nested manner by the 3D printer or other suitable additive manufacturing means.

In one example, pads 60 are then inserted between the outer layer 20 and the mesh layer 30.

In one example, one or both of the outer layer 20 and the mesh layer 30 are be formed in a multi-coloured pattern, in order to make the orthosis 10 more visually appealing to the infant wearer. In addition or alternatively, a surface print, embossed pattern or pierced pattern may be applied to the outer layer 20.

In one example, a fabric liner 270 is then formed and inserted into the orthosis 10. In one example, the liner 270 is flexible. In one example, the liner 270 is formed from a breathable material. In one example, the liner 270 is padded. In one example, the liner 270 is formed by sewing. The liner 270 is retained within the orthosis 10 using the attachment means described above, or other suitable attachment means.

A further example of the invention will now be described with reference to FIGS. 14-16. The orthosis 500 has a structure substantially similar to the example orthoses described hereinabove. In addition, the orthosis 500 comprises one or more sensors 510.

The sensor 510 is operable to measure relevant parameters, for example for use in assessing the effectiveness of the orthosis 500 and/or the comfort of the infant wearer. For example, the sensor 510 may measure at least one of the acceleration of the orthosis 500, the temperature in the orthosis 500, the humidity in the orthosis 500 or the spatial position or orientation of the orthosis 500. In a further example, the sensor 510 is configured to measure the distance or depth between the mesh layer 30 and the outer layer 20 of the orthosis 500. Accordingly, the sensor 510 is able determine the growth of the wearer's head. The sensor 510 may additionally or alternatively measure various other biological information, such as the heart rate of the wearer.

It will be understood that the orthosis 500 may comprises a plurality of sensors 510, each operable to monitor one or more of the above-mentioned parameters. Alternatively, a single sensor device 510 may be provided that is operable to measure all of the desired parameters. It will be further understood that the plurality of sensors 510 may be disposed at various locations throughout the orthosis 300, so as to take readings from various locations. It will be further understood that the sensors 510 can be disposed in a position that is optimal for monitoring the required parameter.

Figure 14:
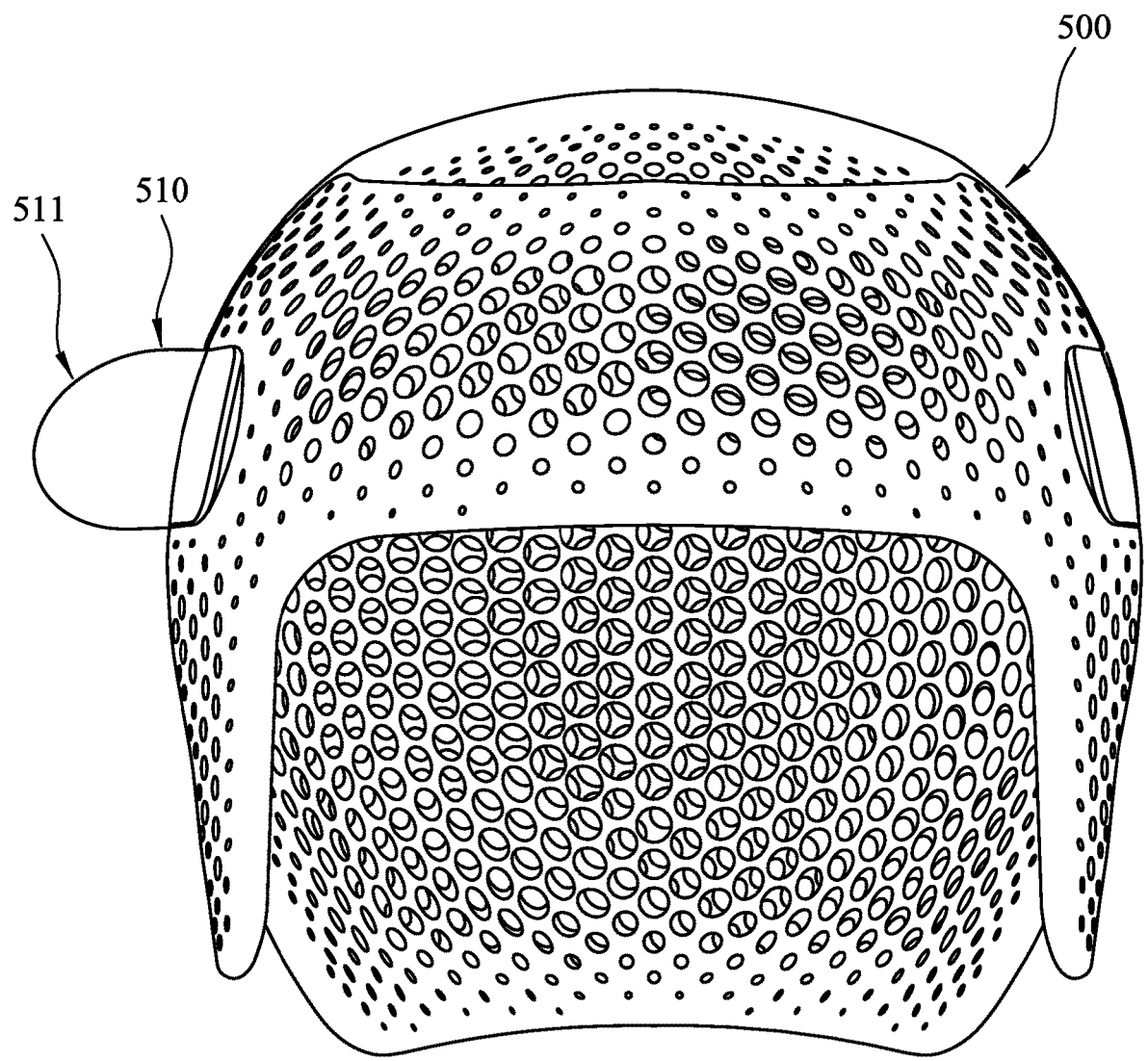
FIG. 14 is a front view of an orthosis according to an embodiment of the invention.
Figure 15:
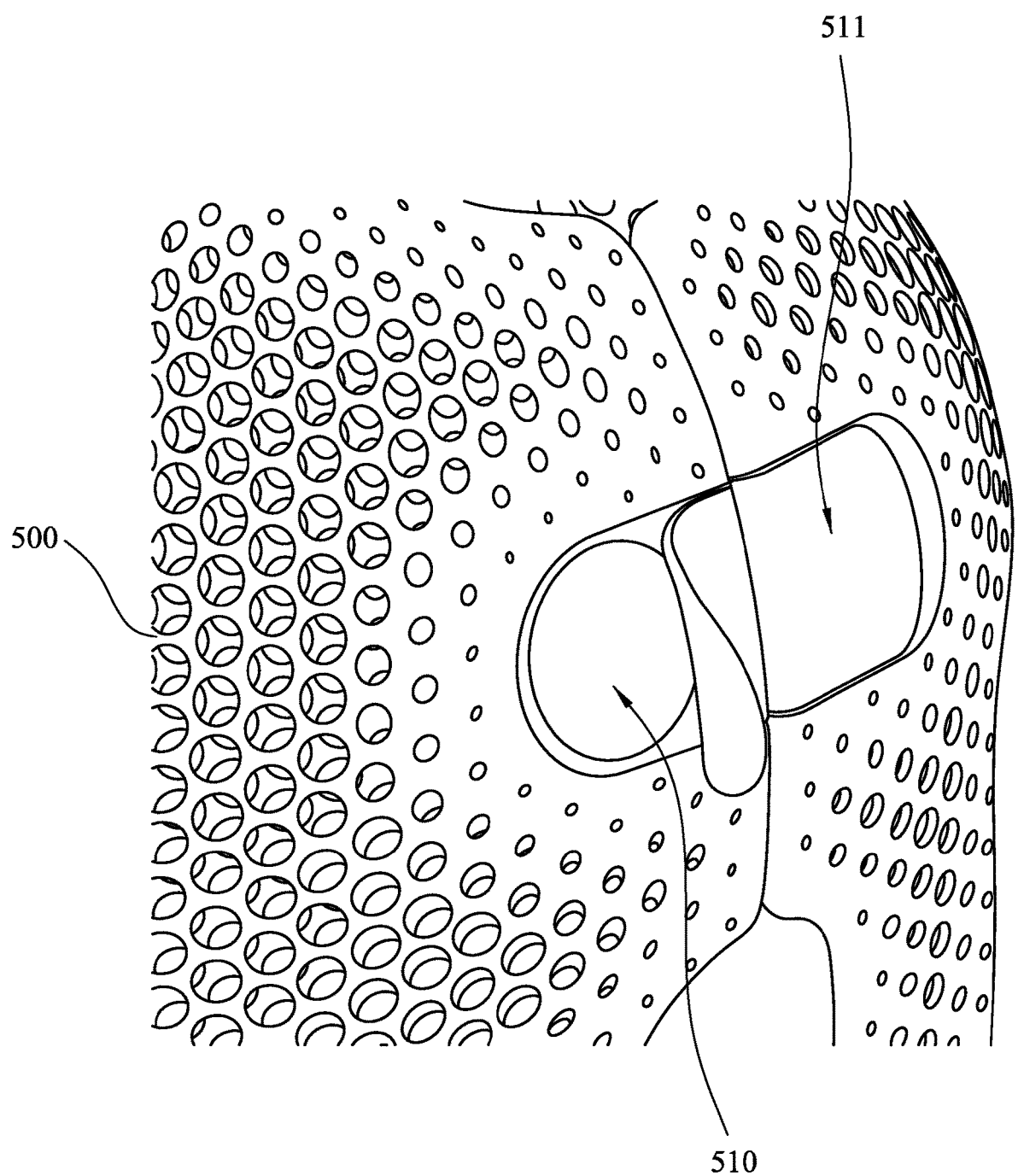
FIG. 15 is an enlarged perspective view of the orthosis of FIG. 14.

In the example shown in FIGS. 14 and 15, the sensor 510 is disposed on the side aspect of the orthosis 500, near the join between the two vertically divided portions. In examples where the orthosis 500 comprises a fastening means such as the fastening means 50, 250 or 450 described above, the sensor 310 may be disposed on the opposite side of the orthosis 300 to the fastening means 50, 250, 450.

In one example, a cover 511 is arranged to cover the sensor 510. In one example, the cover 511 is foldable from a first position, in which the sensor 510 is covered by the cover 511, to a second position, in which the sensor 510 is exposed. The first, covered, position ensures that the sensor 510 cannot be easily accessed, and so prevents damage or accidental removal, for example by the infant wearer. The second, uncovered, position enables access to the sensor 510, for installation, maintenance, replacement and so on. The cover 511 is retained in the first or second position by suitable retaining means, such as hook and loop fasteners or the like.

Figure 16:
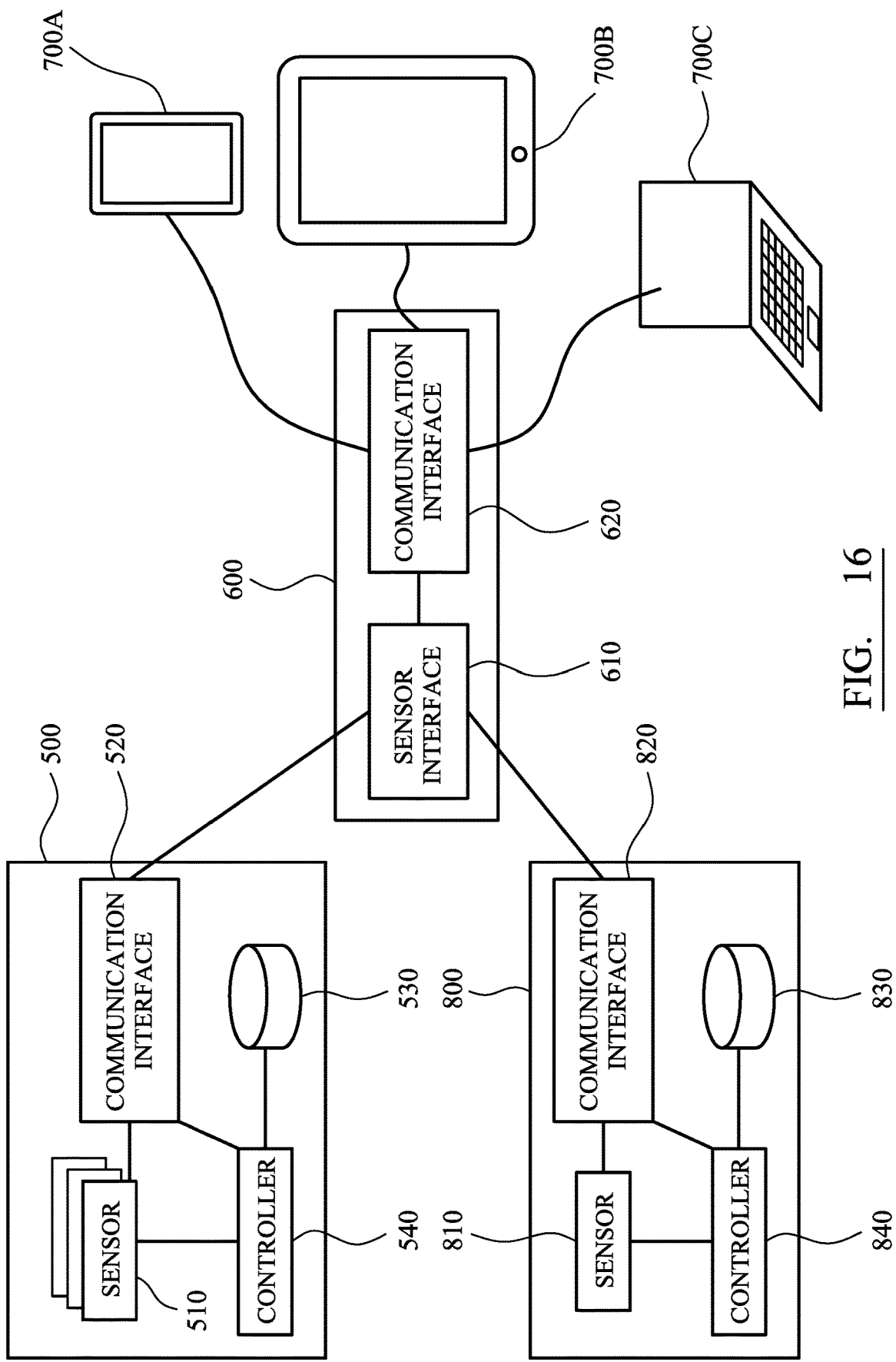
FIG. 16 is a schematic block diagram of an orthosis monitoring system according to an embodiment of the invention.

FIG. 16 is a schematic diagram of an orthosis monitoring system incorporating the orthosis 500, a monitoring device 600 and one or more user devices 700A-C. The orthosis 500 comprises one or more of the sensors 510 as described hereinabove, and a communication interface 520.

The monitoring device 600 is operable to receive sensor readings from the orthosis 500, via a suitable transfer medium. The monitoring device 600 comprises at least one sensor interface 610 and a communication interface 620.

The communication interface 520 is operable to communicate with the sensor interface 610, so as to transfer sensor readings from the orthosis to the monitoring device 600. In one example, the communication interface 520 is passive, and the sensor interface 610 is a reader operable to read the passive sensor. For example, the communication interface 520 and the sensor interface 610 may communicate via a wireless protocol such as Near-field Communication (NFC), Radio-frequency identification (RFID), Bluetooth® Low Energy (BLE) or other short-distance protocols. Accordingly, the sensor interface 610 reads data from the communication interface 520 when it is brought into proximity therewith. In such an example, the monitoring device 600 may conveniently be portable or hand-held, so that it can be easily held close to the orthosis 500, In one example, the monitoring device 600 has multiple sensor interfaces 610 to communicate with multiple sensors 510.

In further examples, the communication interface 520 is active, and actively transmits data to the sensor interface 610. In such an example, the communication interface 520 and sensor interface 610 may communicate via Wi-Fi, Bluetooth®, BLE or via a cable attachable to a port (not shown) on the orthosis 500.

In further examples, the orthosis 500 comprises a memory 530 operable to store a plurality of a sensor readings captured over time. For example, the orthosis 500 may be operable to store sensor readings until the next time the orthosis 500 is connected to the monitoring device 600. Accordingly, sensor readings since the previous connection between the orthosis 500 and monitoring device 600 are retained until such a time that they can be synchronised with the monitoring device 600. In a further example, the orthosis 500 comprises a controller (e.g. a processor or integrated circuit) 540 operable to capture sensor readings at predetermined time intervals and store them in the memory 530. The controller 540 may be further operable to delete stored sensor readings from the memory 530 that have been successfully transferred to the monitoring device.

The communication interface 620 of the monitoring device 600 is operable to transfer the sensor readings to one or more user devices 700A-C. The user devices may take the form of any suitable computing device, such as a smart phone 700A, tablet 700B or personal computer 700C, configured to be used by a parent, therapist or medical professional. The communication interface 620 is operable to transfer the sensor readings over a suitable wireless or wired network connection. For example, the communication interface 620 may transfer the sensor readings via Bluetooth or Wi-Fi.

In a further example, the system comprises a server (not shown), and the server is operable to receive the sensor readings transmitted by the communication interface 620, and store them. In such an example, the user devices 700A-C are then configured to receive the sensor readings from the server.

In one example, each user device 700A-C comprises an application, operable to receive the sensor readings and display them to the user. For example, the application may comprise a graphical user interface, operable to show relevant sensor data. In further examples, the application may store and analyse the sensor readings, for example to generate summary statistics, or to identify the effects of treatment.

In a further example, the system may further include one or more additional sensor devices 800, attachable to other parts of the wearer's body. For example, the sensor devices 800 may be attachable via straps, direct placement on the body part, or by adhesive. In one example, the additional sensor devices 800 comprise positional sensors, operable to determine the spatial position of the sensor device 800. Accordingly, the relative position of various body parts (e.g. limbs) with respect to the head (measured via the sensor 510 of the orthosis 500) can be established. Such measurements advantageously enable parents, carers, physiotherapists, or users directly to monitor the effect of therapy or the effects of the external environment.

Each of the additional sensor devices 800 comprises a sensor 810 and a communication interface 820 substantially the same as the sensor 510 and communication device 510 described above. In further examples, each of the additional sensor devices 800 comprises a memory 830 and controller 840 substantially the same as those described above.

It will be appreciated that the orthosis described herein advantageously comprises a layer that effectively provides resistance in regions where growth is to be restrained and flexibility in regions where growth is to be permitted. Accordingly, a single layer of substantially uniform thickness can correct head deformities such as Flat Head Syndrome or can be used post operatively for infants which have a craniosynostosis. The use of this single layer reduces the bulk of the orthosis, thereby increasing comfort for the wearer.

It will be further appreciated that the construction of the orthosis provides good ventilation for the wearer, thereby reducing issues of overheating and also further increasing comfort for the wearer.

It will also be appreciated that the use of 3D printing to form the mesh layer provides a rapid and convenient mechanism for fabricating a mesh layer suitable for correcting the particular head shape deformities of the individual patient.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features. The invention is not restricted to the details of the foregoing embodiment(s).

The invention extends to any novel one, or any novel combination, of the features disclosed in this specification (including any accompanying claims, abstract and drawings), or to any novel one, or any novel combination, of the steps of any method or process so disclosed.

The invention claimed is:

1. An orthosis for correcting head deformities, the orthosis comprising a mesh layer, wherein regions of varying stiffness in the mesh layer are adapted to apply varying pressure to a wearer's head, so as to restrict undesirable growth and allow desired growth to correct the deformities, and wherein the regions of varying stiffness comprise at least one region of increased flexibility, so as to allow growth of a wearer's head in an area corresponding to the at least one region of increased flexibility.

2. The orthosis of claim 1, wherein the at least one region of increased flexibility comprises a less dense portion of the mesh or a first mesh structure having increased flexibility.

3. The orthosis of claim 1, wherein the mesh layer comprises an auxetic structure.

4. The orthosis of claim 1, further comprising an outer layer that defines the exterior shape of the orthosis, wherein the mesh layer is disposed within the outer layer.

5. The orthosis of claim 4, wherein a surface of the outer layer comprises a plurality of ventilation apertures.

6. The orthosis of claim 4, wherein the mesh layer and the outer layer are arranged such that they are separated by a gap, wherein the gap is under 30 mm.

7. The orthosis of claim 4, comprising a pad disposed between the mesh layer and the outer layer.

8. The orthosis of claim 6, comprising a plurality of cushioning elements, wherein each cushioning element is resiliently deformable in a radial direction with respect to the wearer's head.

9. The orthosis of claim 6, wherein the orthosis comprises two portions and a fastening means to secure the two portions together, so as to secure the orthosis to the wearer's head.

10. The orthosis of claim 6, comprising a liner disposed inside the mesh layer.

11. The orthosis of claim 6, wherein the orthosis comprises a sensor arranged to measure a condition of the orthosis or the wearer and a communication interface, operable to communicate sensor readings measured by the sensor to a monitoring device.

12. The orthosis of claim 11, wherein the condition is at least one of an acceleration of the orthosis, a temperature in the orthosis, a humidity in the orthosis, a spatial or orientation position of the orthosis or a heart rate of the wearer.

13. A method of manufacturing an orthosis for correcting head deformities comprising forming a mesh layer, wherein regions of varying stiffness in the mesh layer are adapted to apply varying pressure to a wearer's head, so as to restrict undesirable growth and allow desired growth to correct the deformities, and wherein the regions of varying stiffness comprise at least one region of increased flexibility, so as to allow growth of a wearer's head in an area corresponding to the at least one region of increased flexibility.

14. The method of claim 13, comprising forming the mesh layer based on a virtual 3D model based on measurements of the wearer's head established by a 3D scan.

15. The method of claim 13, comprising forming the mesh layer using an additive manufacturing means.

16. A computer-readable medium having computer-executable instructions recorded thereon that, when executed, cause a 3D printer to print a mesh layer for an orthosis for correcting head deformities, wherein regions of varying stiffness in the mesh layer are adapted to apply varying pressure to a wearer's head, so as to restrict undesirable growth and allow desired growth to correct the deformities, and wherein the regions of varying stiffness comprise at least one region of increased flexibility, so as to allow growth of a wearer's head in an area corresponding to the at least one region of increased flexibility.

* * * * *